(12) United States Patent
Koshiba

(10) Patent No.: US 6,831,168 B1
(45) Date of Patent: Dec. 14, 2004

(54) ALDEHYDE OXIDASE GENE DERIVED FROM PLANT AND UTILIZATION THEREOF

(75) Inventor: Tomokazu Koshiba, Tokyo (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 08/943,144

(22) Filed: Oct. 3, 1997

(30) Foreign Application Priority Data

Oct. 4, 1996 (JP) .............................................. 8-283314

(51) Int. Cl.$^7$ ............................ C12N 5/10; C12N 5/14; C12N 15/29; C12N 15/52; C12N 15/82
(52) U.S. Cl. .................... 536/23.6; 536/23.1; 536/23.2; 435/320.1; 435/419; 435/468
(58) Field of Search ................................ 536/23.6, 104, 536/23.1, 23.2; 435/419, 69.1, 468, 410; 800/205, 278, 281, 295, 320.1

(56) References Cited

PUBLICATIONS

Harms et al., Expression of a Felx Allene Oxide Synthase cDNA Leads t Increased Encodgenous Jasmonic Acid (JA) Levels in Transgenic . . . , Oct. 1995, The Plant Cell, vol. 7, pp. 1645–1654.*
Luca et al., Molecular characterization of secondary metobolic pathways, 1993, New and Information, vol. 5, No. 6, pp. 225N–229N.*
Troubleshooting RACE Reactions.*
Napoli et al. 1990. The Plant Cell. vol. 279–289.*
Finnegan and McElroy. 1994. Bio/Technology. 12: 883–885.*
Matzke and Matzke. 1995. Plant Physiol. 107:679–685.*
Mehta et al. Protein Expression and Purification. 1997. vol. 11: 86–94.*
Ejdback et al. Protein Expression and Purification. 1997. vol. 11: 17–25.*
Berger and Kimmel. Methods in Enzymology 1987.*
Liu et al. P.N.A.S. 1994. vol. 1888–1892.*
Felsted et al. The Journal of Biological Chemistry 1973. 1vol. 248: 2580–2587.*
Koshiba, Tomokazu et al., "Purification and Properties of Flavin– and Molybdenum–Containing Aldehyde Oxidase from Coleoptiles of Maize," *Plant Physiol.* (1996) vol. 110, pp. 781–789.
Sekimoto, Hiroyuki et al., "Cloning and Molecular Characterization of Plant Aldehyde Oxidase," *The Journal Of Biological Chemistry* (Jun. 13, 1997) vol. 272, No. 24, pp. 15280–15285.

* cited by examiner

*Primary Examiner*—Amy J. Nelson
*Assistant Examiner*—Russell Kallis
(74) *Attorney, Agent, or Firm*—Birch, Stewart, Kolasch & Birch LLP

(57) ABSTRACT

There is provided an aldehyde oxidase gene which is a 4.4 kbp gene obtainable from a plant and which encodes an amino acid sequence of an enzyme capable of oxidizing an aldehyde compound to a carboxylic acid and utilization thereof.

13 Claims, No Drawings

ALDEHYDE OXIDASE GENE DERIVED FROM PLANT AND UTILIZATION THEREOF

FIELD OF THE INVENTION

The present invention relates to an aldehyde oxidase gene derived from a plant and utilization thereof.

It has been known that a natural plant growth hormone auxin alternatively IAA or indoleacetic acid is produced from tryptophane via indoleacetaldehyde followed by the action of anoxidase in higher plants. The hormone is deeply involved in various morphogenesis and environmental adaptation of a plant by its physiological activity and has significant effects on maturing by growth acceleration in general crop cultivation, improvement in yield and in quality by rooting acceleration in nursery plant production, increase in yield by growth acceleration of fruits in fruit vegetable cultivation, increase in added value by acceleration of flowering and elongation of life by prevention of defoliation or aging in ornamental plant cultivation. Therefore, there has been a strong demand for a method for artificially controlling the said enzyme for industry and particularly agricultural production.

Under these circumstances, the present inventors have successfully determined the total amino acid sequence and gene of the enzyme and completed the present invention.

Thus, the present invention provides:

1) An aldehyde oxidase gene which is a 4.4 Kbp gene obtainable from a plant and which encodes an amino acid sequence of an enzyme capable of oxidizing an aldehyde compound to a carboxylic acid (hereinafter, referred to as the gene of the present invention),
2) The aldehyde oxidase gene according to item 1), wherein the aldehyde compound is indoleacetaldehyde and the carboxylic acid is indoleacetic acid,
3) The aldehyde oxidase gene according to item 1 or 2 which is derived from a maize plant (*Zea mays* L.),
4) The aldehyde oxidase gene according to item 1 which is a nucleotide sequence encoding an amino acid sequence shown by SEQ ID NO: 2,
5) The aldehyde oxidase gene according to item 4 which has a nucleotide sequence shown by SEQ ID NO: 1 (loci of CDS being 46 . . . 4120),
6) The aldehyde oxidase gene according to item 1 which is a nucleotide sequence encoding an amino acid sequence shown by SEQ ID NO: 4,
7) The aldehyde oxidase gene according to item 6 which has a nucleotide sequence shown by SEQ ID NO: 3 (loci of CDS being 91 . . . 4138),
8) A plasmid comprising the aldehyde oxidase gene according to item 1, 2, 3, 4, 5, 6 or 7,
9) A transformant transformed by introducing the plasmid according to item 8 into a host cell,
10) The transformant according to item 9, wherein the host cell is a microorganism,
11) The transformant according to item 9, wherein the host cell is a plant,
12) A process for constructing an expression plasmid which comprises ligating:
    (1) a promoter capable of functioning in a plant cell,
    (2) an aldehyde oxidase gene according to item 1, 2, 3, 4, 5, 6 or 7 and
    (3) a terminator capable of functioning in a plant in a functional manner and in the said order described above,
13) An expression plasmid comprising:
    (1) a promoter capable of functioning in a plant cell,
    (2) an aldehyde oxidase gene according to item 1, 2, 3, 4, 5, 6 or 7 and
    (3) a terminator capable of functioning in a plant which are ligated in a functional manner and in the said order described above,
14) A process for controlling production of an aldehyde oxidase in a transformant which comprises introducing, into a host cell, an expression plasmid comprising:
    (1) a promoter capable of functioning in a plant cell,
    (2) an aldehyde oxidase gene and
    (3) a terminator capable of functioning in a plant which are ligated in a functional manner and in the said order described above to transform said host cell,
15) The process according to item 14, wherein the aldehyde oxidase gene is derived from a plant and the host cell is a plant, and
16) The process according to item 14, wherein the expression plasmid is the expression plasmid according to item 13.

EMBODIMENTS OF THE INVENTION

The present invention will be described in more detail.

The gene of the present invention comprises about 4.4 kbp nucleotide obtainable from a plant and is an aldehyde oxidase gene that encodes an amino acid sequence of an enzyme capable of oxidizing an aldehyde compound to generate a carboxylic acid. For example, it is capable of oxidizing indoleacetaldehyde to generate indoleacetic acid.

The gene of the present invention can be obtained from a plant, for example, maize or the like. The gene of the present invention and the enzyme as the translation product of it have an action of oxidizing an acetaldehyde compound to a carboxylic acid in a cell. Said enzyme may also act, for example, on benzaldehyde, butyraldehyde, protocatechualdehyde or the like as the substrate, in addition to indolealdehyde of course, a single enzyme may act on plural compounds as substrates.

The gene of the present invention specifically includes, for example, a gene which is a nucleotide sequence encoding an amino acid sequence shown by SEQ ID NO: 2 and a gene which is a nucleotide equence encoding an amino acid sequence shown by SEQ ID NO: 4 as well as an equivalent of them. The expression "an equivalent of them" used herein means an aldehyde oxidase gene having a nucleotide sequence of an aldehyde oxidase gene that encodes an amino acid sequence shown by SEQ ID NO: 2 kor SEQ ID NO: 4 with a single nucleotide or plural nucleotides added, deleted or replaced, and refers to a DNA which is an analog having the same function. More particularly, this includes a gene having a nucleotide sequence shown by SEQ ID NO: 1 (loci of CDS being 46 . . . 4120) or a nucleotide sequence shown by SEQ ID NO: 3 (loci of CDS being 91 . . . 4138).

The gene of the present invention can be obtained by the following process.

For example, seeds of Golden Cross Bantam 70 (purchased from Sakata-no-tane), a maize cultivar, are subjected to a treatment for hastening of germination by immersing overnight in running tap water, subsequently seeded on a paper towel moistened with water and placed in red light (0.8 W/m$^2$) under a condition of 25° C. for 2 days and then in the dark for 1 day to allow germination. Top portions of young sheaths grown to 1.0–1.5 cm from the obtained seedlings are excised under a green safety light, immediately frozen with liquid nitrogen and stored at −30° C. as samples for purification of enzymes and samples for extracting RNAs.

For purifying aldehyde oxidase from the frozen samples prepared in this manner, it is appropriate to use a method described in T. Koshiba et al., Plant Physiology, 1996, 110, 781–789.

In order to prevent decrease in activity of the enzyme and decomposition of the protein during procedures of extraction and purification, it is preferred to carry out all the treatments in the purification steps at a lower temperature of 2–4° C., as is ordinary manner in such procedures. First, 150–200 g of the frozen sample is taken as a material for one batch of purification. The material is mechanically crushed by a homogenizer or the like with addition of 400 ml of 0.1 M phosphate buffer (pH 7.4) and centrifuged at 12,000 g for 30 minutes. The supernatant is separated as a crude enzyme standard sample. From the crude enzyme standard sample, a fraction is obtained with 30–50% saturated ammonium sulfate, dialyzed against 20 mM Tris HCl buffer (pH 8.0) and centrifuged at 20,000 g for 20 minutes. The supernatant from centrifugation is passed over an ion-exchange column (for example, DEAE TOYOPEARL 650 M, manufactured by Tosoh) and a fraction with an aldehyde oxidase activity is collected. Said fraction with the specific activity is subjected to chromatography with a hydrophobic column, a hydroxyapatite column and an ion-exchange column (for example, DEAE-5PM) in this order and purified until the fraction with aldehyde oxidase activity is detected as an almost single protein band by silver staining after electrophoresis.

According to the above described purification procedure, about 2,000 times purification, in terms of the amount of protein in the crude enzyme standard sample, is usually possible. It can be confirmed that the finally purified protein has a size of about 300 kD in molecular weight by the gel filtration column process. Further, it can be detected as a band having a size of about 150 kD in molecular weight by SDS polyacrylamide gel electrophoresis (SDS-PAGE), indicating that said enzyme forms a dimer.

In the above described fractionating process by column chromatography, effective collection of the fraction with aldehyde oxidase activity can be achieved making use of measurement of aldehyde oxidase activity in respective fractions. For this purpose, a method in which indoleacetaldehyde is added to the purified fraction as a substrate and the amount of produced indoleacetic acid is determined by HPLC, for example, can be utilized. Precisely, 100 µl of reaction solution consisting of 5–50 µl of the purified fraction, 0.1 mM indoleacetaldehyde and 0.1 mM phosphate buffer (pH 7.4) is prepared. The solution is incubated at 30° C. for 30 minutes to effect the reaction and, immediately after, 8 µl of 1 N HCl, 5 µl of 2.0 M sodium hydrogen sulfite and 50 µl of methanol are added to the solution to quench the reaction. The reaction solution is centrifuged at 15,000 g for 5 minutes and 100 µl of the obtained supernatant is taken as a analytical sample for HPLC. By detecting absorption at 280 nm, indoleacetaldehyde as the substrate and indoleacetic acid as the reaction product can be quantitatively analyzed. It is effective to carry out HPLC with, for example, ODS C18 column and to elute with 20–50% linear gradient of methanol containing 0.1% acetic acid.

The protein obtained in this manner is partially digested and the digested peptide is analyzed to obtain a partial amino acid sequence information. Usually, the purified aldehyde oxidase sample is separated by SDS-PAGE and a protein band of 150 kD is collected by excision. The collected gel fragments are treated, for example, with Achromobacter Protease I (API) in the presence of 0.1% SDS and digested peptide fragments are extracted. This is loaded, for example, on a reverse phase HPLC accompanied by a pre-column of an anion exchanger (DEAE) to separate peptides and recover them. The amino acid sequences are determined by a protein sequencer and parts of the samples are subjected to molecular weight determination by MALDI-TOF to check accuracy of the obtained amino acid sequence information.

Then, an oligo DNA expected to encode the amino acid sequence is synthesized on the basis of the obtained amino acid sequence information. Further, RT-PCR is conducted using a total RNA as a template to amplify cDNA partial fragment, which is then cloned into a plasmid vector.

For extraction of the total RNA, 7 g of the frozen sample, for example, is triturated in liquid nitrogen with a mortar and a pestle to form fine powders. After evaporating liquid nitrogen, RNA is extracted by the conventional manner, for example, using guanidine thiocyanate/cesium chloride process and the total RNA is collected from the extract by ethanol precipitation. By this procedure, usually 1 mg of the total RNA is obtained.

For amplification of cDNA, a reverse transcription reaction is carried out using, among synthetic oligo DNAs, one synthesized in antisense orientation as a primer and binding it to a transcription product of a target RNA contained in the total RNA. The reverse transcription reaction can be conducted using a commercially available reverse transcription PCR kit, for example, RNA-PCR kit (manufacturedbyPerkin-ElmerCetusInstruments). Then,the obtained reverse transcription product can be subjected again to PCR in which an oligo DNA synthesized in sense orientation is added to amplify cDNA fragment.

The obtained cDNA amplification fragment is purified and cloned into a plasmid vector. As the plasmid vector, for example, pCRII (manufactured by Invitrogen) can be used and cDNA amplification fragment can be cloned by transforming E. coli according to the conventional manner and screening transformants having an insert. The nucleotide sequence of the clone is determined using, for example, ABI PRISM Dye Primer Cycle Sequencing Ready Reaction Kits (manufactured by Applied Biosystems) on the obtained cDNA clone.

Sense and antisense primers for part of nucleotide sequence in cDNA partial fragment obtained in this manner can be synthesized and subjected to RACE to obtain cDNA fragments having terminals in 5'-orientation and 3'-orientation, respectively. A complete length cDNA can be obtained by ligating them and cloning into a plasmid vector. For the RACE, a commercially available Marathon cDNA Amplification Kit (manufactured by Clontech), for example, can be used.

The gene of the present invention can be utilized in the following manner.

For example, a host cell such as a microorganism, a plant or the like is transformed by introducing the gene of the present invention to form a transformant.

In order to introduce and express the gene of the present invention in a plant cell, an expression plasmid comprising (1) a promoter capable of functioning in a plant cell, (2) a gene of the present invention (an aldehyde oxidase gene described in items 1 to 7 above) and (3) a terminator capable of functioning in a plant cell which are ligated in a functional manner in a plant cell and in the said order described above and introduced in a plant cell to transform said cell.

The expression "in a functional manner" used herein means that, when the constructed plasmid is introduced into a plant cell to transform it, the gene of the present invention is integrated under the control of a promoter such that the gene is normally transcribed/translated and have a function of expressing a protein in said plant cell.

The promoter capable of functioning in a plant cell includes, for example, T-DNA derived constitutive type promoters such as nopaline synthase gene (NOS) promoter, octopine synthase gene (OCS) promoter and the like, plant virus derived promoters such as cauliflower mosaic virus (CaMV) derived 18S and 35S promoters and the like, and inducible type promoters such as phenylalanine ammonialyase (PAL) gene promoter, chalcone synthase (CHS) gene promoter, pathogen-related (PR) gene promoter and the like. Further, it includes other known plant promoters.

The terminator capable of functioning in a plant cell includes, for example, T-DNA derived constitutive type terminators such as nopaline synthase gene (NOS) terminator and the like, plant virus derived terminators such as garlic virus GV1, GV2 terminators and the like. Further, it includes other known plant terminators.

For transforming a plant cell by introducing such plasmid into a plant cell, the above described expression plasmid is introduced into a plant cell by any of conventional means such as Agrobacterium infection method (JP-B-2-58917 and JP-A-60-70080), electroporation method into protoplast (JP-A-60-251887 and JP-A-5-68575), particle gun method (JP-A-508316 and JP-A-63-258525) and the like, and a transformed plant cell can be obtained by selecting a plant cell into which the gene of the present invention is introduced. The transformed plant is obtained by regenerating a plant according to a conventional plant cell culturing process, for example, described in Uchimiya, Manual for Plant Gene Manipulation (Method for Producing Transgenic Plants), Published by Kodansha Scientific (ISBN 4-06-153515-7 C3045), 1990, pages 27–55.

Further, the present invention provides a process for controlling production of an aldehyde oxidase in a transformant which comprises introducing, into a host cell, an expression plasmid comprising (1) a promoter capable of functioning in a plant cell, (2) an aldehyde oxidase gene and (3) a terminator capable of functioning in a plant which are ligated in a functional manner and in the said order described above to transform said host cell.

The promoter capable of functioning in a plant cell includes, for example, lacZ gene promoter of lactose operon in E. coli, alcohol dehydrogenase gene (ADH) promoter in yeast, Adenovirus major late (Ad.ML) promoter, early promoter of SV 40, Baculovirus promoter and the like. When the host is a plant, promoters capable of functioning in a plant as described above may also be included.

The terminator capable of functioning in a plant cell includes, for example, HIS terminator sequence in yeast, ADHI terminator, early splicing region of SV 40 and the like. When the host is a plant, terminators capable of functioning in a plant as described above may also be included.

The aldehyde oxidase gene may be any one insofar as it is a gene encoding an amino acid sequence of an enzyme capabre of oxidizing an aldehyde compound to form a carboxylic acid. This includes, for example, aldehyde oxidase genes derived from plants and preferably the gene of the present invention (an aldehyde oxidase gene described in items 1 to 7 above).

Transformation of a host cell by introducing such plasmid into said host cell can be effected by a method generally used in the field of genetic engineering.

When the host cell is a plant cell, it can be effected, for example, by a method generally used in the field of plant genetic engineering and the field of plant tissue cultivation as described above.

The transformation of a plant by introducing the gene of the present invention may bring about enhancement of generally known physiological action of auxin or supression of the same. For example, by enhancing the activity of auxin through a sense gene, elongation growth and differentiation to vascular bundle of the host cell can be accelerated resulting in growth acceleration of a plant and enhanced capacity of storing assimilation products. As a result, early maturing of crops, enlargement of harvest such as fruits and improvement in yield or quality can be expected and realized. To the contrary, by suppressing the activity of auxin through a sense gene, spindly growth of a plant is prevented and a plant capable of growing under improper environmental conditions such as insufficient insolation can be bred. Further, by adequately controlling growth, dwarfing of crops becomes possible and application, for example, to prevention of lodging of rice plants and shortening of cut flowers become possible. As a result, improvement in yield and quality can be expected.

Addition of hormone to the medium is generally essential for aseptic cultivation of cells or tissue of a plant. When auxin activity in a plant is enhanced by introducing and expressing the gene of the present invention thereby increasing production of aldehyde oxidase in a transformant, said plant is expected to be in a state in which capacity of cell proliferation, differentiation and individual regeneration in the sterile culture is enhanced. Therefore, it is possible to create a so-called easily cultured strain and this is useful in the production of nursery plant of virus-free crops for which tissue culture-nucleotide mass culture is conducted and garden crops such as flower and ornamental plants.

EXAMPLES

The present invention will now be described in more detail by means of Examples. It is to be understood, however, that the scope of the present invention is not limited to these Examples.

Example 1

Preparation of Maize Young Sheath

Seeds of Golden Cross Bantam 70 (purchased from Sakata-no-tane), a maize cultivar, were subjected to a treatment for hastening of germination by immersing overnight in running tap water, subsequently seeded on a paper towel moistened with water and placed in red light (0.8 W/m$^2$) under a condition of 25° C. for 2 days and then in the dark for 1 day to allow germination. Top portions (1.0–1.5 cm) of young sheaths grown from the obtained seedlings to 2–3 cm were excised under a green safety light, immediately frozen with liquid nitrogen and stored at −30° C.

Example 2

Preparation of Aldehyde Oxidase

All the procedures in the following purification steps were conducted at a low temperature of 2–4° C.

First, about 200 g of the frozen sample prepared in Example 1 was taken as a material for one batch of purification The material was mechanically crushed by a homogenizer with addition of 400 ml of 0.1 M phosphate buffer (pH 7.4) and centrifuged at 12,000 g for 30 minutes. The supernatant was separated as a crude enzyme standard sample. Subsequently, from the crude enzyme standard sample, a fraction was obtained with 30–50% saturated ammonium sulfate, dialyzed against 20 mM Tris HCl buffer (pH 8.0) and centrifuged at 20,000 g for 20 minutes. The supernatant from centrifugation was passed over an ion-exchange column (DEAE TOYOPEARL 650 M, manufactured by Tosoh) and a fraction with an aldehyde oxidase activity was collected on the basis of activity measurement conducted in a manner described below in Example 3. Said fraction with activity was subjected to chromatography with a hydrophobic column, a hydroxyapatite column and an on-exchange column (DEAE-5PM) in this order and purified until the fraction with aldehyde oxidase activity was detected as an almost single protein band by silver staining on electrophoresis.

By the above described purification procedure, about 0.09 mg of protein was recovered from 1,873 mg of protein in the crude enzyme standard sample, and ratio of enzyme activity for aldehyde oxidase to the original was 1,950 times. It was confirmed that the finally purified protein had a size of about 300 kD in molecular weight by the gel filtration column process. Further, it was detected as a band having a size of about 150 kD in molecular weight by SDS polyacrylamide gel electrophoresis (SDS-PAGE), indicating that said enzyme formed a dimer.

Example 3

Method for Measuring Aldehyde Oxidase Activity

Measurement of aldehyde oxidase activity in the respective purified fractions described in Example 2 was carried out by a method in which indoleacetaldehyde was added to the purified fraction as a substrate and the amount of produced indoleacetic acid (IAA) was determined by HPLC. The reaction was carried out with 100 μl of reaction solution consisting of 5–50 μl of the purified fraction, 0.1 mM indoleacetaldehdeand 0.1 mM phosphate buffer (pH 7.4). The solution was incubated at 30° C. for 30 minutes and, immediately after, 8 μl of 1 N HCl, 5 μl of 2.0M sodium hydrogen sulfite and 50 μl of methanol were added to the solution to quench the reaction. The reaction solution was centrifuged at 15,000 g for 5 minutes and 100 μl of the obtained supernatant was taken as an analytical sample for HPLC. By detecting absorption at 280 nm, indoleacetaldehyde and indoleacetic acid were quantitatively analyzed. HPLC was carried out with ODS C18 column and eluted with 20–50% linear gradient of methanol containing 0.1% acetic acid.

Example 4

Peptide Digestion of Aldehyde Oxidase: Partial Amino Acid Sequence)

The purified protein obtained in Example 2 was separated by SDS-PAGE and a protein band of 150 kD was collected by excision. The collected gel fragments were reacted with Achromobacter Protease I (API) in the presence of 0.1% SDS and digested peptide fragments were extracted. This was passed over a reverse phase HPLC accompanied by a pre-column of an anion exchanger (DEAE) to separate peptides, which were collected. The amino acid sequences were determined by a protein sequencer (ABI 477A).

As a result, the following 4 sequences were obtained as the partial amino acid sequences.

The first one was a sequence, shown below, having 18 amino acid residues:

Gln Val Asn Asp Val Pro Ile Ala Ala Ser Gly Asp Gly Trp Tyr His Pro Lys and it was confirmed that the sequence corresponded to NOS. 235 to 252 residues in the amino acid sequence shown by SEQ ID NO: 2.

The second one was a sequence, shown below, having 16 a mino acid residues:

Thr Asn Ser Asp Gly Leu Val Ile His Asp Gly Thr Trp Thr Tyr Lys and it was confirmed that the sequence corresponded to 1,234 to 1,249 residues in the amino acid sequence shown by SEQ ID NO: 2 or to 1,226 to 1,241 residues in the amino acid sequence shown by SEQ ID NO: 4.

The third one was a sequence, shown below, having 20 amino acid residues:

Ser Ile Glu Glu Leu His Arg Leu Phe Asp Ser Ser Trp Phe Asp Asp Ser Ser Val Lys and it was confirmed that the sequence corresponded to Nos. 253 to 272 residues in the amino acid sequence shown by SEQ ID NO: 2.

The fourth one was a sequence, shown below, having 21 amino acid residues:

Val Gly Ala Glu Ile Gln Ala Ser Gly Glu Ala Val Tyr Val Asp Asp Ile Pro Ala Pro Lys and it was confirmed that the sequence corresponded to Nos. 591 to 611 residues in the amino acid sequence shown by SEQ ID NO: 2.

Parts of these digested peptide samples were subjected to molecular weight determination by MALDI-TOF to check accuracy of the obtained amino acid sequence.

Example 5

Preparation of Total RNA From Maize Young Sheath and Synthesis of cDNA

In a manner similar to that in Example 1, seeds of maize were germinated and 7 g of top portions of the young sheath were collected from seedlings. These were frozen in 10 ml of liquid nitrogen and triturated with a mortar and a pestle to form fine powders. After evaporating liquid nitrogen, RNA was extracted by the conventional manner (guanidine thiocyanate/cesium chloride method) and 1 mg of the total RNA was collected from the extract by ethanol precipitation.

Example 6

Preparation of an Oligo DNA Primer and RT-PCR

A mixture of oligo DNAs expected to encode the partial amino acid sequence determined in Example 4 was synthesized in both sense and antisense orientation.

Specifically, as a nucleotide sequence expected from 8 amino acid residues: Val Ile His Asp Gly Thr Trp Thr in the partial amino acid sequence 2 described in Example 4, a 23-mer in antisense orientation: 5'-GTCCAIGTICC(AG)TC(AG)TGIATIAC-3' SEQ ID NO: 5 was synthesized.

Further, as a nucleotide sequence expected from 8 amino acid residues: Gly Glu Ala Val Tyr Val Asp Asp in the partial amino acid sequence 4 described in Example 4, a 23-mer in sense orientation: 5'-GGIGA(AG)GCIGTITA(TC)GTIGA(TC)GA-3' SEQ ID NO: 6 was synthesized.

A reverse transcription reaction was carried out using, among them, one synthesized in antisense orientation as a primer and a commercially available reverse transcription PCR kit (RNA-PCR kit, manufactured by Perkin-Elmer Cetus Instruments). Then, the obtained reverse transcription product was subjected again to PCR in which an oligo DNA synthesized in sense orientation was added. As the result, amplification of cDNA fragment was confirmed.

Example 7

Cloning of the PCR-amplified Fragment Into a Vector and Analysis of the Structure)

The amplified cDNA fragment obtained in Example 6 was purified and cloned into a plasmid vector pCRII (manufactured by Invitrogen). Further, the nucleotide sequence of the insert in said plasmid vector was determined by 373A DNA Sequencer (manufactured by Applied Biosystems) using ABI PRISM Dye Primer Cycle Sequencing Ready Reaction Kits (manufactured by Applied Biosystems) and the structure of said cDNA fragment was determined. As a result, it was revealed that the cloned cDNA fragment contained 2 kinds having different structure, one corresponding to Nos. 1,839 to 3,785 nucleotides in the nucleotide sequence shown by SEQ ID NO: 1 and the other corresponding to Nos. 1,858 to 3,806 nucleotides in the nucleotide sequence shown by SEQ ID NO: 3.

Example 8

Isolation of a Complete Length cDNA Clone

Based on the nucleotide sequence information obtained in Example 7, nucleotide sequences specific for said 2 cDNAs, respectively, were searched and oligo DNAs for the parts were synthesized in sense and antisense orientations.

Specifically, as the sense oligo DNAs corresponding to the nucleotide sequence shown by SEQ ID NO: 1, two kinds: a 28-mer: 5'-GCTGGTCAAAATATT-GGTGTCGTGATTG-3' (common) (SEQ ID NO: 7), and a 28-mer: 5'-GATTGCTGAAACACAAAGATATGCTAAT-3' (SEQ ID NO: 8), and as the antisense oligo DNAS, four kinds: a 27-mer: 5'-TGGCTGCAGATTTT-CTGTGCTATACTC-3' (common) (SEQ ID NO: 9), a 27-mer: 5'-TGCTTTGCAGCCATATTAGCTATCTT-3' (SEQ ID NO: 10), a 24-mer: 5'-ACAGCCTTTTGG-AAGCCACCTGGA-3' (SEQ ID NO: 11), and a 24-mer: 5'-ATCGGACTTGTTGTCGGCCTTGAC-3' (SEQ ID NO: 12) were synthesized.

Also, as the sense oligo DNAs corresponding to the nucleotide sequence shown by SEQ ID NO: 3, two kinds: a 28-mer: 5'-GCTGGTCAAAATATTGGTGTCGTGATTG-3' (common) (SEQ ID NO: 7), and a 28-mer: 5'-GATTGCTCAAACACAGAAGTATGCCTAC-3' (SEQ ID NO: 13), and as the antisense oligo DNAs, three kinds: a 27-mer: 5'-TGGCTGCAGATTTTCTGTGCTATACTC-3' (common) (SEQ ID NO: 9), a 25-mer: 5'-CTTTGCCGCCATGTAGGCATACTTC-3' (SEQ ID NO: 14), and a 24-mer: 5'-TTCCACCTATGGTTGC-AGTGTTCC-3'(SEQ ID NO: 15) were synthesized.

Using them as primers, RACE process was carried out with a commercially available Marathon cDNA Amplification Kit (manufactured by Clontech) to obtain cDNA fragments having terminals in 5'-orientation and 3'-orientation, respectively. Further, a complete length cDNA was obtained by ligating them and cloned into a plasmid vector pCRII (manufactured by Invitrogen).

Example 9

Analysis of Nucleotide Sequence and Determination of Amino Acid Sequence of cDNA Clones For-two cDNA clones obtained in Example 8, analysis of nucleotide sequence was carried out with 373A DNA Sequencer (manufactured by Applied Biosystem) using ABI PRISM Dye Primer Cycle Sequencing Ready Reaction Kits, Dye Terminator Cycle Sequencing Kits (manufactured by Applied Biosystems). As a result, it was revealed that the genes of the present invention were cDNAs having 4,412 bp and 4,359 bp, respectively (see SEQ ID NOS: 1 and 3).

Further, based upon said nucleotide sequence, the total amino acid sequences encoded by the genes of the present invention were determined with GENETYX Gene Analysis Software (manufactured by SDC, Software Development Co.). It was revealed that they were proteins having 1,358 and 1,349 amino acid residues, respectively (see SEQ ID NOS: 2 and 4).

Example 10

Construction of Aldehyde Oxidase Expression Plasmid for Direct Introduction)

In order to allow expression of the gene of the present invention derived from maize by introducing in a plant cell, the following direct introduction expression vector for plant, for example, is constructed.

A GUS expression vector pBI221 (manufactured by Clontech) derived from pUC19 is digested by restriction enzymes SmaI and SacI (both being manufactured by Takara Shuzo) and 2.8 Kbp fraction is recovered removing GUS structural gene. The terminus is blunted with T4 DNA polymerase (manufactured by Takara Shuzo). Then, the terminus is treated for de-phosphorylation with bacterial alkaline phosphatase (manufactured by Takara Shuzo).

On the other hand, the complete length cDNA obtained in Example 8 is prepared for an insert gene and the terminus is blunted with T4 DNA polymerase in a similar manner. Afterwards, the both are ligated with T4 DNA ligase (DNA Ligation Kit Ver. 2, manufactured by Takara Shuzo) and used for transforming competent cells of E. coli HB101 strain (manufactured by Takara Shuzo), from which Ampicillin resistant strains are selected. Among the recombinant plasmid amplified from the selected strains, clones in which a coding region for the aldehyde oxidase is inserted in normal orientation in relation to 35S promoter derived from cauliflower mosaic virus and the terminator derived from nopaline synthase and cloned in which said region is inserted in reverse orientation are selected and taken as expression vectors for direct introduction, respectively.

Example 11

Construction of Aldehyde Oxidase Expression Plasmid for Indirect Introduction In order to allow expression of the aldehyde oxidase gene derived from maize by introducing in a plant cell, the following indirect introduction expression vector for plant, for example, is constructed.

In a manner similar to that in Example 10, the aldehyde oxidase gene of which the terminus is blunted is prepared for an insert gene. On the other hand, a GUS expression binary vector pBI121 (manufactured by Clontech) derived from pBIN19 is digested by restriction enzymes SmaI and SacI and a fraction is recovered removing GUS structural gene. The terminus is blunted in a similar manner and treated for de-phosphorylation. The both are ligated and used for transforming E. coli. The recombinant plasmid are selected and taken as aldehyde oxidase expression vectors for indirect introduction. Further, the plasmid vectors are transferred to the strain Agrobacterium tumefaciens LBA4404 by the tri-parental method ( GUS gene fusion system, manufactured by Clontech).

Example 12

Creation of a Transformed Plant by Introducing Aldehyde Oxidase Expression Plasmid; Part 1

The expression vectors for direct introduction obtainable in Example 10 are introduced by a particle gun into an aseptically cultured immature scutellum of rice plant according to a method described in Shimada et al., Ikushugaku Zasshi, 1994, 44 Supplement 1, 66, to obtain transformed rice plants. Similarly, they are introduced by a particle gun into an aseptically cultured immature scutellum of wheat plant according to a method described in Takumi et al., Ikushugaku Zasshi, 1995, 45 Supplement 1, 57, to obtain transformed wheat plants. Similarly, they are introduced by a particle gun into an aseptically cultured immature scutellum of barley plant according to a method described in Hagio et al., Ikushugaku Zasshi, 1994, 44 Supplement 1, 67, to obtain transformed barley plants. Similarly, they are introduced by particle gun into an adventitious embryo of maize according to a method described in M. E. Fromm et al., Bio/Technology, 1990, 8, 833–839, to obtain transformed maize plants. Further, the expression vectors for direct introduction obtained in Example 10 are introduced by a particle gun into an adventitious embryo of soybean according to a method described in Japanese Patent Application Hei 3-291501 to obtain transformed soybean plants.

Example 13

Creation of a Transformed Plant by Introducing Aldehyde Oxidase Expression Plasmid; Part 2

The strains from *Agrobacteriuffl tumefaciens* LBA4404 into which the aldehyde oxidase expression vectors for indirect introduction are introduced, obtainable in Example 11, are infected to an aseptically cultured leaf of tobacco by a method described in Uchimiya, Manual for Plant Gene Manipulation (Method for Producing Transgenic Plants), Published by Kodansha Scientific (ISBN4-06-153513-7), 1990, pages 27–33, to obtain transformed tobacco plants. Similarly, they are infected to a petiole of an aseptically cultured seedling of carrot by a method described in N. Pawlicki et al., Plant Cell, Tissue and Organ Culture, 1992, 31, 129–139, to obtain transformed carrot plants. Further, they are infected to a hypocotyl or cotyledon of an aseptically cultured seedling of Lotus corniculatus by a method described in Nagasawa et al., Ikushugaku Zasshi, 1995, 45 Supplement 1, 143, to obtain transformed Lotus corniculatus plants. Similarly, they are infected to an aseptically cultured adventitious embryo of alfalfa by a method described in R. Desgagnes et al., Plant Cell, Tissue and Organ Culture, 1995, 42, 129–140, to obtain transformed alfalfa plants. Similarly, they are infected to an epicotyl or cotyledon of an aseptically cultured seedling of pea by a method described in J. Pounti-Kaerlas et al., Theoretical and Applied Genetics, 1990, 80, 246–252, to obtain transformed pea plants.

---

What is claimed is:

1. An isolated polynucleotide encoding an aldehyde oxidase enzyme, wherein said enzyme oxidizes an aldehyde compound to a carboxylic acid, and wherein said polynucleotide has a sequence selected from the group consisting of:
   (a) a nucleotide sequence encoding the amino acid sequence of SEQ ID NO: 2;
   (b) the nucleotide sequence of SEQ ID NO: 1;
   (c) a nucleotide sequence encoding the amino acid sequence of SEQ ID NO: 4;
   (d) the nucleotide sequence of SEQ ID NO: 3 and
   (e) a maize nucleotide sequence of about 4.4 Kbp.

2. The isolated polynucleotide according to claim 1, wherein the aldehyde compound is indoleacetaldehyde and the carboxylic acid is indoleacetic acid.

3. A plasmid comprising a polynucleotide encoding an aldehyde oxidase enzyme, wherein said enzyme oxidizes an aldehyde compound to a carboxIylic acid, and wherein said polynucleotide has a sequence selected from the group consisting of:
   (a) a nucleotide sequence encoding the amino acid sequence of SEQ ID NO: 2;
   (b) the nucleotide sequence of SEQ ID NO: 1;
   (c) a nucleotide sequence encoding the amino acid sequence of SEQ ID NO: 4;
   (d) the nucleotide sequence of SEQ ID NO: 3 and
   (e) a maize nucleotide sequence of about 4.4 Kbp.

4. A transformed host cell comprising the plasmid according to claim 3.

5. The transformed host cell according to claim 4, wherein the host cell is a microorganism.

6. The transformed host cell according to claim 4, wherein the host cell is a plant cell.

7. A process of constructing an expression plasmid which comprises ligating in a functional manner
   (1) a promoter capable of functioning in a plant cell upstream from,
   (2) a polynucleotide encoding an aldehyde oxidase enzyme, wherein said enzyme oxidizes an aldehyde compound to a carboxylic acid, and wherein said polynucleotide has a sequence selected from the group consisting of:
- (a) a nucleotide sequence encoding the amino acid sequence of SEQ ID NO: 2;
- (b) the nucleotide sequence of SEQ ID NO: 1;
- (c) a nucleotide sequence encoding the amino acid sequence of SEQ ID NO: 4;
- (d) the nuclcotide sequence of SEQ ID NO: 3 and
- (e) a maize nucleotide sequence of about 4.4 Kbp.

(3) a terminator functional in a plant downstream from the polynucleotide of (2).

8. An expression plasmid comprising:

(1) a promoter capable of functioning in a plant cell, (2) a polynucleotide encoding an aldehyde oxidase enzyme, wherein said enzyme oxidizes an aldehyde compound to a carboxylic acid, and wherein said polynucleotide has a sequence selected from the group consisting of:
- (a) a nucleotide sequence encoding an amino acid sequence shown by SEQ ID NO: 2;
- (b) a nucleotide sequence shown by SEQ ID NO: 1;
- (c) a nucleotide sequence encoding an amino acid sequence shown by SEQ ID NO: 4;
- (d) a nucleotide sequence shown by SEQ ID. NO: 3; and
- (e) a nucleotide sequence encoding an amino acid sequence of about a 4.4 Kbp gene obtainable from a maize plant (*Zea mays L*), wherein said gene of about 4.4 Kbp is amplifiable with a combination of a PCR primer selected from the group consisting of SEQ ID NO: 7, SEQ ID NO: 8, and SEQ ID NO: 13 and a PCR primer selected from the group consisting of SEQ ID NO: 9, SEQ ID NO: 10, SEQ ID NO: 11, SEQ ID NO: 12, SEQ ID NO: 14, and SEQ ID NO: 15, and (3) a terminator capable of functioning in a plant which are ligated in a functional manner and in the order described above.

9. A process for producing aldehyde oxidase in a transformed host cell which comprises introducing into a host cell an expression plasmid comprising:

(1) a promoter functional in a plant cell upstream from, (2) a polynucleotide encoding an aldehyde oxidase enzyme wherein said enzyme oxidizes an aldehyde compound to a carboxylic acid, and wherein said polynucleotide has a sequence selected from the group consisting of:
- (a) a nucleotide sequence encoding the amino acid sequence of SEQ ID NO: 2;
- (b) the nucleotide sequence of SEQ ID NO: 1;
- (c) a nucleotide sequence encoding the amino acid sequence of SEQ ID NO: 4;
- (d) the nucleotide sequence of SEQ ID NO: 3 and
- (e) a maize nucleotide sequence of about 4.4 Kbp, and (3) a terminator functional in a plant and downstream from the polynucleotide of (2), which are ligated in a functional manner to transform said host cell whereby the production of aldehyde oxidase of the transformed host cell is controlled.

10. The process according to claim 9, wherein the host cell is a plant cell.

11. An isolated polynucleotide encoding an aldehyde oxidase enzyme comprising the amino acid sequence of SEQ ID NO: 2.

12. An isolated polynucleotide encoding an aldehyde oxidase enzyme comprising the amino acid sequence of SEQ ID NO: 4.

13. An isolated polynucleotide encoding an aldehyde oxidase enzyme, wherein said polynucleotide has the nucleotide sequence of SEQ ID NO: 1 or SEQ ID NO: 3.

* * * * *

SEQUENCE LISTING

```
(1) GENERAL INFORMATION:

(iii) NUMBER OF SEQUENCES: 15

(2) INFORMATION FOR SEQ ID NO:1:

(i) SEQUENCE CHARACTERISTICS:
        (A) LENGTH: 4412 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: maize (Zea mays L.)
        (B) STRAIN: cultivar: Golden Cross Bantam 70

(ix) FEATURE:
        (A) NAME/KEY: CDS
        (B) LOCATION: 46..4119

(xi) SEQUENCE DESCRIPTION: SEQ ID NO:1:

GTGCTGTGTT GTGCTGTGCT GCGTGCTGTG GAGGGGGAGG AGGAG ATG GGG AAG       54
                                                 Met Gly Lys
                                                   1

GAG GCA GGG GCA GCG GAG TCG TCG ACG GTG GTG CTG GCC GTC AAC GGC   102
Glu Ala Gly Ala Ala Glu Ser Ser Thr Val Val Leu Ala Val Asn Gly
    5                  10                  15

AAG CGC TAC GAG GCG GCC GGC GTG GCT CCG TCC ACG TCG CTG CTG GAG   150
Lys Arg Tyr Glu Ala Ala Gly Val Ala Pro Ser Thr Ser Leu Leu Glu
 20                  25                  30                  35
```

-continued

| | |
|---|---|
| TTC CTC CGC ACC CAG ACG CCC GTC AGA GGC CCC AAG CTC GGC TGC GGC<br>Phe Leu Arg Thr Gln Thr Pro Val Arg Gly Pro Lys Leu Gly Cys Gly<br>          40              45              50 | 198 |
| GAA GGT GGC TGC GGT GCA TGC GTG GTC CTC GTC TCC AAG TAC GAC CCG<br>Glu Gly Gly Cys Gly Ala Cys Val Val Leu Val Ser Lys Tyr Asp Pro<br>      55              60              65 | 246 |
| GCC ACG GAC GAG GTG ACC GAG TTC TCT GCC AGC TCC TGC CTG ACG CTG<br>Ala Thr Asp Glu Val Thr Glu Phe Ser Ala Ser Ser Cys Leu Thr Leu<br>          70              75              80 | 294 |
| CTC CAC AGC GTG GAC CGC TGC TCA GTG ACC ACC AGC GAG GGA ATC GGC<br>Leu His Ser Val Asp Arg Cys Ser Val Thr Thr Ser Glu Gly Ile Gly<br>      85              90              95 | 342 |
| AAC ACC AGG GAT GGC TAC CAC CCC GTG CAG CAG CGC CTC TCC GGC TTC<br>Asn Thr Arg Asp Gly Tyr His Pro Val Gln Gln Arg Leu Ser Gly Phe<br>100             105             110             115 | 390 |
| CAC GCC TCG CAG TGC GGC TTC TGC ACA CCC GGC ATG TGC ATG TCC ATC<br>His Ala Ser Gln Cys Gly Phe Cys Thr Pro Gly Met Cys Met Ser Ile<br>          120             125             130 | 438 |
| TTC TCC GCC CTT GTC AAG GCC GAC AAC AAG TCC GAT CGC CCG GAC CCT<br>Phe Ser Ala Leu Val Lys Ala Asp Asn Lys Ser Asp Arg Pro Asp Pro<br>      135             140             145 | 486 |
| CCT GCT GGC TTC TCC AAG ATC ACT ACC TCG GAG GCA GAG AAG GCT GTC<br>Pro Ala Gly Phe Ser Lys Ile Thr Thr Ser Glu Ala Glu Lys Ala Val<br>          150             155             160 | 534 |
| TCG GGC AAC CTT TGT CGT TGC ACC GGA TAC AGA CCC ATT GTT GAC ACC<br>Ser Gly Asn Leu Cys Arg Cys Thr Gly Tyr Arg Pro Ile Val Asp Thr<br>      165             170             175 | 582 |
| TGC AAA AGC TTT GCC TCT GAT GTT GAC CTC GAG GAC CTA GGC CTC AAC<br>Cys Lys Ser Phe Ala Ser Asp Val Asp Leu Glu Asp Leu Gly Leu Asn<br>180             185             190             195 | 630 |
| TGT TTC TGG AAG AAG GGC GAA GAA CCT GCA GAA GTC AGC AGG CTG CCG<br>Cys Phe Trp Lys Lys Gly Glu Glu Pro Ala Glu Val Ser Arg Leu Pro<br>          200             205             210 | 678 |
| GGG TAC AAC AGC GGT GCC GTC TGC ACC TTT CCA GAG TTT CTC AAA TCC<br>Gly Tyr Asn Ser Gly Ala Val Cys Thr Phe Pro Glu Phe Leu Lys Ser<br>      215             220             225 | 726 |
| GAA ATC AAG TCT ACT ATG AAG CAG GTG AAC GAT GTC CCC ATT GCA GCC<br>Glu Ile Lys Ser Thr Met Lys Gln Val Asn Asp Val Pro Ile Ala Ala<br>          230             235             240 | 774 |
| TCA GGT GAT GGC TGG TAC CAT CCT AAG AGC ATT GAA GAG CTT CAC AGG<br>Ser Gly Asp Gly Trp Tyr His Pro Lys Ser Ile Glu Glu Leu His Arg<br>      245             250             255 | 822 |
| TTG TTT GAT TCC AGC TGG TTT GAT GAC AGT TCT GTG AAG ATT GTT GCT<br>Leu Phe Asp Ser Ser Trp Phe Asp Asp Ser Ser Val Lys Ile Val Ala<br>260             265             270             275 | 870 |
| TCA AAC ACT GGG TCT GGA GTG TAC AAG GAT CAG GAC CTC TAC GAC AAG<br>Ser Asn Thr Gly Ser Gly Val Tyr Lys Asp Gln Asp Leu Tyr Asp Lys<br>          280             285             290 | 918 |
| TAC ATT GAC ATC AAA GGA ATC CCA GAG CTT TCA GTC ATC AAT AAA AAC<br>Tyr Ile Asp Ile Lys Gly Ile Pro Glu Leu Ser Val Ile Asn Lys Asn<br>      295             300             305 | 966 |
| GAC AAA GCA ATT GAG CTT GGA TCA GTT GTG TCC ATC TCT AAA GCT ATT<br>Asp Lys Ala Ile Glu Leu Gly Ser Val Val Ser Ile Ser Lys Ala Ile<br>          310             315             320 | 1014 |
| GAA GTG CTG TCA GAT GGA AAT TTG GTC TTC AGA AAG ATT GCT GAT CAC<br>Glu Val Leu Ser Asp Gly Asn Leu Val Phe Arg Lys Ile Ala Asp His<br>      325             330             335 | 1062 |
| CTC AAC AAA GTG GCT TCA CCG TTT GTT CGG AAC ACT GCA ACC ATA GGA<br>Leu Asn Lys Val Ala Ser Pro Phe Val Arg Asn Thr Ala Thr Ile Gly | 1110 |

-continued

```
                340                 345                 350                 355
GGA AAC ATA ATG ATG GCA CAA AGG TTG CCA TTT GAA TCG GAT GTT GCA     1158
Gly Asn Ile Met Met Ala Gln Arg Leu Pro Phe Glu Ser Asp Val Ala
                    360                 365                 370

ACC GTG CTC CTA GCT GCG GGT TCG ACA GTC ACA GTC CAG GTG GCT TCC     1206
Thr Val Leu Leu Ala Ala Gly Ser Thr Val Thr Val Gln Val Ala Ser
                375                 380                 385

AAA AGG CTG TGC TTC ACT CTG GAG GAA TTC TTG GAA CAA CCT CCA TGT     1254
Lys Arg Leu Cys Phe Thr Leu Glu Glu Phe Leu Glu Gln Pro Pro Cys
            390                 395                 400

GAT TCT AGG ACC CTG CTG CTG AGC ATA TTT ATC CCA GAA TGG GGT TCA     1302
Asp Ser Arg Thr Leu Leu Leu Ser Ile Phe Ile Pro Glu Trp Gly Ser
        405                 410                 415

GAC TAT GTC ACC TTT GAG ACT TTC CGA GCC GCC CCA CGA CCA TTT GGA     1350
Asp Tyr Val Thr Phe Glu Thr Phe Arg Ala Ala Pro Arg Pro Phe Gly
420                 425                 430                 435

AAT GCT GTC TCT TAT GTA AAC TCT GCT TTC TTG GCA AGG ACA TCA GGC     1398
Asn Ala Val Ser Tyr Val Asn Ser Ala Phe Leu Ala Arg Thr Ser Gly
                440                 445                 450

AGC CTT CTA ATT GAG GAT ATA TGC TTG GCA TTT GGT GCC TAC GGA GTC     1446
Ser Leu Leu Ile Glu Asp Ile Cys Leu Ala Phe Gly Ala Tyr Gly Val
            455                 460                 465

GAT CAT GCC ATC AGA GCT AAG AAG GTT GAA GAT TTC TTG AAG GGA AAA     1494
Asp His Ala Ile Arg Ala Lys Lys Val Glu Asp Phe Leu Lys Gly Lys
        470                 475                 480

TCG CTG AGC TCA TTT GTG ATA CTT GAA GCA ATT AAA CTA CTC AAA GAT     1542
Ser Leu Ser Ser Phe Val Ile Leu Glu Ala Ile Lys Leu Leu Lys Asp
    485                 490                 495

ACC GTT TCA CCA TCA GAA GGC ACT ACA CAT CAT GAA TAC AGG GTC AGC     1590
Thr Val Ser Pro Ser Glu Gly Thr Thr His His Glu Tyr Arg Val Ser
500                 505                 510                 515

TTG GCT GTC AGT TTC TTG TTC AGT TTC TTA TCT TCC CTT GCC AAC AGT     1638
Leu Ala Val Ser Phe Leu Phe Ser Phe Leu Ser Ser Leu Ala Asn Ser
                520                 525                 530

TCG AGT GCA CCA TCA AAT ATT GAT ACT CCC AAT GGG TCA TAT ACT CAT     1686
Ser Ser Ala Pro Ser Asn Ile Asp Thr Pro Asn Gly Ser Tyr Thr His
            535                 540                 545

GAA ACT GGT AGC AAT GTG GAC TCA CCT GAG AGG CAT ATT AAG GTT GAC     1734
Glu Thr Gly Ser Asn Val Asp Ser Pro Glu Arg His Ile Lys Val Asp
        550                 555                 560

AGC AAT GAT TTG CCA ATT CGT TCA AGA CAA GAA ATG GTT TTC AGC GAT     1782
Ser Asn Asp Leu Pro Ile Arg Ser Arg Gln Glu Met Val Phe Ser Asp
    565                 570                 575

GAG TAC AAG CCT GTT GGC AAG CCG ATC AAG AAA GTC GGG GCA GAG ATC     1830
Glu Tyr Lys Pro Val Gly Lys Pro Ile Lys Lys Val Gly Ala Glu Ile
580                 585                 590                 595

CAA GCA TCA GGG GAG GCT GTG TAC GTT GAT GAT ATC CCT GCT CCC AAG     1878
Gln Ala Ser Gly Glu Ala Val Tyr Val Asp Asp Ile Pro Ala Pro Lys
                600                 605                 610

GAT TGC CTC TAT GGA GCA TTT ATC TAC AGC ACA CAT CCT CAT GCT CAT     1926
Asp Cys Leu Tyr Gly Ala Phe Ile Tyr Ser Thr His Pro His Ala His
            615                 620                 625

GTG AGA AGT ATC AAC TTC AAA TCA TCC TTG GCT TCA CAG AAG GTC ATC     1974
Val Arg Ser Ile Asn Phe Lys Ser Ser Leu Ala Ser Gln Lys Val Ile
        630                 635                 640

ACA GTT ATA ACC GCA AAG GAT ATT CCA AGC GGT GGA GAA AAT ATT GGA     2022
Thr Val Ile Thr Ala Lys Asp Ile Pro Ser Gly Gly Glu Asn Ile Gly
    645                 650                 655

AGC AGC TTC CTG ATG CAA GGA GAA GCA CTA TTT GCA GAT CCA ATC GCT     2070
```

```
                Ser Ser Phe Leu Met Gln Gly Glu Ala Leu Phe Ala Asp Pro Ile Ala
                660                 665                 670                 675

GAA TTT GCT GGT CAA AAT ATT GGT GTC GTG ATT GCT GAA ACA CAA AGA              2118
Glu Phe Ala Gly Gln Asn Ile Gly Val Val Ile Ala Glu Thr Gln Arg
                        680                 685                 690

TAT GCT AAT ATG GCT GCA AAG CAA GCT GTT GTT GAG TAT AGC ACA GAA              2166
Tyr Ala Asn Met Ala Ala Lys Gln Ala Val Val Glu Tyr Ser Thr Glu
                695                 700                 705

AAT CTG CAG CCA CCA ATT CTG ACA ATA GAA GAT GCC ATC CAA AGA AAC              2214
Asn Leu Gln Pro Pro Ile Leu Thr Ile Glu Asp Ala Ile Gln Arg Asn
            710                 715                 720

AGC TAC ATC CAA ATT CCC CCA TTT TTA GCT CCA AAG CCA GTT GGT GAC              2262
Ser Tyr Ile Gln Ile Pro Pro Phe Leu Ala Pro Lys Pro Val Gly Asp
        725                 730                 735

TAC AAC AAA GGG ATG GCT GAA GCA GAC CAC AAG ATT CTA TCA GCA GAG              2310
Tyr Asn Lys Gly Met Ala Glu Ala Asp His Lys Ile Leu Ser Ala Glu
740                 745                 750                 755

GTA AAA CTT GAA TCC CAG TAC TAC TTC TAC ATG GAA ACT CAA GCA GCA              2358
Val Lys Leu Glu Ser Gln Tyr Tyr Phe Tyr Met Glu Thr Gln Ala Ala
                760                 765                 770

CTA GCG ATT CCT GAT GAA GAT AAC TGC ATA ACA ATC TAT TCC TCG ACA              2406
Leu Ala Ile Pro Asp Glu Asp Asn Cys Ile Thr Ile Tyr Ser Ser Thr
                    775                 780                 785

CAA ATG CCT GAG CTC ACA CAA AAT TTG ATA GCA AGG TGT CTT GGC ATT              2454
Gln Met Pro Glu Leu Thr Gln Asn Leu Ile Ala Arg Cys Leu Gly Ile
            790                 795                 800

CCA TTT CAC AAT GTC CGT GTC ATC AGC AGA AGA GTA GGA GGA GGC TTT              2502
Pro Phe His Asn Val Arg Val Ile Ser Arg Arg Val Gly Gly Gly Phe
        805                 810                 815

GGT GGA AAG GCA ATG AAA GCA ACG CAT ACT GCA TGT GCA TGT GCC CTT              2550
Gly Gly Lys Ala Met Lys Ala Thr His Thr Ala Cys Ala Cys Ala Leu
820                 825                 830                 835

GCT GCC TTC AAG CTG CGG CGT CCA GTT AGG ATG TAC CTC GAT CGC AAG              2598
Ala Ala Phe Lys Leu Arg Arg Pro Val Arg Met Tyr Leu Asp Arg Lys
                840                 845                 850

ACG GAC ATG ATA ATG GCT GGA GGG AGA CAT CCA ATG AAG GCG AAG TAC              2646
Thr Asp Met Ile Met Ala Gly Gly Arg His Pro Met Lys Ala Lys Tyr
                    855                 860                 865

TCT GTT GGG TTC AAG TCA GAT GGC AAG ATC ACA GCC TTG CAC CTA GAT              2694
Ser Val Gly Phe Lys Ser Asp Gly Lys Ile Thr Ala Leu His Leu Asp
            870                 875                 880

CTT GGA ATC AAT GCT GGA ATA TCA CCA GAT GTG AGT CCA TTG ATG CCA              2742
Leu Gly Ile Asn Ala Gly Ile Ser Pro Asp Val Ser Pro Leu Met Pro
        885                 890                 895

CGT GCT ATC ATA GGA GCT CTC AAA AAG TAC AAC TGG GGC ACT CTT GAA              2790
Arg Ala Ile Ile Gly Ala Leu Lys Lys Tyr Asn Trp Gly Thr Leu Glu
900                 905                 910                 915

TTT GAC ACC AAG GTC TGC AAG ACA AAT GTC TCA TCA AAG TCA GCA ATG              2838
Phe Asp Thr Lys Val Cys Lys Thr Asn Val Ser Ser Lys Ser Ala Met
                920                 925                 930

CGA GCT CCT GGA GAT GTG CAG GGC TCT TTC ATC GCT GAA GCC ATC ATC              2886
Arg Ala Pro Gly Asp Val Gln Gly Ser Phe Ile Ala Glu Ala Ile Ile
                    935                 940                 945

GAG CAT GTT GCC TCA GCA CTC GCA CTA GAC ACT AAC ACC GTC AGG AGG              2934
Glu His Val Ala Ser Ala Leu Ala Leu Asp Thr Asn Thr Val Arg Arg
            950                 955                 960

AAG AAC CTT CAT GAT TTT GAA AGC CTT GAA GTT TTC TAT GGA GAA AGT              2982
Lys Asn Leu His Asp Phe Glu Ser Leu Glu Val Phe Tyr Gly Glu Ser
        965                 970                 975
```

```
GCA GGT GAA GCT TCT ACA TAC AGC CTG GTT TCC ATG TTT GAC AAG CTG    3030
Ala Gly Glu Ala Ser Thr Tyr Ser Leu Val Ser Met Phe Asp Lys Leu
980             985                 990                 995

GCC TTG TCT CCA GAA TAC CAG CAC AGG GCT GCA ATG ATT GAG CAG TTC    3078
Ala Leu Ser Pro Glu Tyr Gln His Arg Ala Ala Met Ile Glu Gln Phe
            1000                1005                1010

AAT AGC AGC AAC AAA TGG AAG AAA CGC GGC ATT TCT TGT GTG CCA GCC    3126
Asn Ser Ser Asn Lys Trp Lys Lys Arg Gly Ile Ser Cys Val Pro Ala
        1015                1020                1025

ACT TAT GAG GTT AAT CTT CGA CCA ACT CCA GGC AAG GTG TCA ATC ATG    3174
Thr Tyr Glu Val Asn Leu Arg Pro Thr Pro Gly Lys Val Ser Ile Met
    1030                1035                1040

AAT GAT GGT TCC ATC GCT GTC GAG GTT GGA GGA ATT GAG ATA GGT CAA    3222
Asn Asp Gly Ser Ile Ala Val Glu Val Gly Gly Ile Glu Ile Gly Gln
1045                1050                1055

GGA TTG TGG ACT AAA GTG AAG CAG ATG ACG GCC TTT GGA CTG GGA CAG    3270
Gly Leu Trp Thr Lys Val Lys Gln Met Thr Ala Phe Gly Leu Gly Gln
1060                1065                1070                1075

CTG TGT CCT GAT GGT GGC GAA TGC CTT CTG GAC AAG GTT CGG GTT ATC    3318
Leu Cys Pro Asp Gly Gly Glu Cys Leu Leu Asp Lys Val Arg Val Ile
            1080                1085                1090

CAG GCA GAC ACA TTA AGC CTG ATC CAA GGA GGT ATG ACT GCT GGG AGC    3366
Gln Ala Asp Thr Leu Ser Leu Ile Gln Gly Gly Met Thr Ala Gly Ser
        1095                1100                1105

ACC ACT TCT GAA ACT AGC TGT GAA ACA GTT CGG CAA TCT TGT GTT GCA    3414
Thr Thr Ser Glu Thr Ser Cys Glu Thr Val Arg Gln Ser Cys Val Ala
    1110                1115                1120

CTG GTT GAG AAG CTG AAC CCT ATC AAG GAG AGT CTC GAA GCT AAG TCC    3462
Leu Val Glu Lys Leu Asn Pro Ile Lys Glu Ser Leu Glu Ala Lys Ser
1125                1130                1135

AAC ACA GTG GAA TGG AGT GCC TTG ATT GCT CAG GCA AGC ATG GCG AGT    3510
Asn Thr Val Glu Trp Ser Ala Leu Ile Ala Gln Ala Ser Met Ala Ser
1140                1145                1150                1155

GTG AAC CTA TCA GCA CAG CCG TAC TGG ACT CCT GAT CCA TCT TTC AAG    3558
Val Asn Leu Ser Ala Gln Pro Tyr Trp Thr Pro Asp Pro Ser Phe Lys
            1160                1165                1170

AGC TAC TTG AAC TAC GGA GCT GGC ACC AGT GAG GTG GAA GTT GAT ATC    3606
Ser Tyr Leu Asn Tyr Gly Ala Gly Thr Ser Glu Val Glu Val Asp Ile
        1175                1180                1185

CTA ACA GGA GCA ACC ACA ATT CTG CGA AGC GAC CTG GTG TAT GAC TGC    3654
Leu Thr Gly Ala Thr Thr Ile Leu Arg Ser Asp Leu Val Tyr Asp Cys
    1190                1195                1200

GGG CAG AGC CTA AAC CCT GCT GTA GAC TTG GGC CAG ATC GAG GGC TGC    3702
Gly Gln Ser Leu Asn Pro Ala Val Asp Leu Gly Gln Ile Glu Gly Cys
1205                1210                1215

TTT GTC CAA GGA ATA GGG TTC TTC ACG AAC GAG GAC TAC AAG ACG AAT    3750
Phe Val Gln Gly Ile Gly Phe Phe Thr Asn Glu Asp Tyr Lys Thr Asn
1220                1225                1230                1235

TCC GAC GGG TTG GTC ATC CAC GAC GGC ACA TGG ACG TAC AAG ATC CCC    3798
Ser Asp Gly Leu Val Ile His Asp Gly Thr Trp Thr Tyr Lys Ile Pro
            1240                1245                1250

ACG GTG GAT AAT ATC CCG AAG GAG TTC AAT GTT GAG ATG TTT AAC AGC    3846
Thr Val Asp Asn Ile Pro Lys Glu Phe Asn Val Glu Met Phe Asn Ser
        1255                1260                1265

GCC CCT GAC AAG AAG CGT GTC CTA TCT TCC AAA GCG TCG GGC GAG CCG    3894
Ala Pro Asp Lys Lys Arg Val Leu Ser Ser Lys Ala Ser Gly Glu Pro
    1270                1275                1280

CCG CTG GTT CTC GCA ACC TCG GTG CAC TGC GCG ATG AGG GAG GCC ATC    3942
Pro Leu Val Leu Ala Thr Ser Val His Cys Ala Met Arg Glu Ala Ile
1285                1290                1295
```

-continued

```
AGG GCG GCG AGG AAG GAG TTC TCG GTC AGC ACC AGC CCC GCG AAA TCC      3990
Arg Ala Ala Arg Lys Glu Phe Ser Val Ser Thr Ser Pro Ala Lys Ser
1300                1305                1310                1315

GCC GTC ACA TTC CAG ATG GAC GTG CCG GCG ACG ATG CCT GTC GTC AAG      4038
Ala Val Thr Phe Gln Met Asp Val Pro Ala Thr Met Pro Val Val Lys
            1320                1325                1330

GAG CTC TGC GGC CTC GAC GTC GTG GAG AGG TAC CTC GAG AAC GTG TCT      4086
Glu Leu Cys Gly Leu Asp Val Val Glu Arg Tyr Leu Glu Asn Val Ser
        1335                1340                1345

GCC GCC AGT GCC GGC CCA AAC ACA GCG AAA GCA TAGATCCAGC AGGCCTCAGG    4139
Ala Ala Ser Ala Gly Pro Asn Thr Ala Lys Ala
            1350                1355

GTGCAGTCGG CGCACTGCCA GAGATGATGT GTGCTGCCCT GATGTACAGA CAGTACAGTA    4199

CAGAGGAGAG AGAATTGGGG GAACTCAGGA ACTGCGAGGA GCGATGAACA GTATATAGAG    4259

TGAAAAATAA AAGTGCTTCG TACTAATAAT CACTAGAAAA AATTATGCAC ATCTCCCACG    4319

CACTACCGGC ACGACTGTTG AATATTTTGT AAAATAAGAT GTCATAAGCT ATTTATTTTC    4379

TGTAAAAAAA AAAAAAAAAA AAAAAAAAAA AAA                                 4412

(2) INFORMATION FOR SEQ ID NO:2:

(i) SEQUENCE CHARACTERISTICS:
        (A) LENGTH: 1358 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Lys Glu Ala Gly Ala Ala Glu Ser Ser Thr Val Val Leu Ala
1               5                   10                  15

Val Asn Gly Lys Arg Tyr Glu Ala Ala Gly Val Ala Pro Ser Thr Ser
            20                  25                  30

Leu Leu Glu Phe Leu Arg Thr Gln Thr Pro Val Arg Gly Pro Lys Leu
        35                  40                  45

Gly Cys Gly Glu Gly Gly Cys Gly Ala Cys Val Val Leu Val Ser Lys
    50                  55                  60

Tyr Asp Pro Ala Thr Asp Glu Val Thr Glu Phe Ser Ala Ser Ser Cys
65                  70                  75                  80

Leu Thr Leu Leu His Ser Val Asp Arg Cys Ser Val Thr Thr Ser Glu
            85                  90                  95

Gly Ile Gly Asn Thr Arg Asp Gly Tyr His Pro Val Gln Gln Arg Leu
            100                 105                 110

Ser Gly Phe His Ala Ser Gln Cys Gly Phe Cys Thr Pro Gly Met Cys
        115                 120                 125

Met Ser Ile Phe Ser Ala Leu Val Lys Ala Asp Asn Lys Ser Asp Arg
130                 135                 140

Pro Asp Pro Pro Ala Gly Phe Ser Lys Ile Thr Thr Ser Glu Ala Glu
145                 150                 155                 160

Lys Ala Val Ser Gly Asn Leu Cys Arg Cys Thr Gly Tyr Arg Pro Ile
            165                 170                 175

Val Asp Thr Cys Lys Ser Phe Ala Ser Asp Val Asp Leu Glu Asp Leu
            180                 185                 190

Gly Leu Asn Cys Phe Trp Lys Lys Gly Glu Glu Pro Ala Glu Val Ser
        195                 200                 205

Arg Leu Pro Gly Tyr Asn Ser Gly Ala Val Cys Thr Phe Pro Glu Phe
```

-continued

```
            210                 215                 220
Leu Lys Ser Glu Ile Lys Ser Thr Met Lys Gln Val Asn Asp Val Pro
225                 230                 235                 240

Ile Ala Ala Ser Gly Asp Gly Trp Tyr His Pro Lys Ser Ile Glu Glu
                245                 250                 255

Leu His Arg Leu Phe Asp Ser Ser Trp Phe Asp Asp Ser Ser Val Lys
                260                 265                 270

Ile Val Ala Ser Asn Thr Gly Ser Gly Val Tyr Lys Asp Gln Asp Leu
                275                 280                 285

Tyr Asp Lys Tyr Ile Asp Ile Lys Gly Ile Pro Glu Leu Ser Val Ile
290                 295                 300

Asn Lys Asn Asp Lys Ala Ile Glu Leu Gly Ser Val Val Ser Ile Ser
305                 310                 315                 320

Lys Ala Ile Glu Val Leu Ser Asp Gly Asn Leu Val Phe Arg Lys Ile
                325                 330                 335

Ala Asp His Leu Asn Lys Val Ala Ser Pro Phe Val Arg Asn Thr Ala
                340                 345                 350

Thr Ile Gly Gly Asn Ile Met Met Ala Gln Arg Leu Pro Phe Glu Ser
                355                 360                 365

Asp Val Ala Thr Val Leu Leu Ala Ala Gly Ser Thr Val Thr Val Gln
                370                 375                 380

Val Ala Ser Lys Arg Leu Cys Phe Thr Leu Glu Glu Phe Leu Glu Gln
385                 390                 395                 400

Pro Pro Cys Asp Ser Arg Thr Leu Leu Leu Ser Ile Phe Ile Pro Glu
                405                 410                 415

Trp Gly Ser Asp Tyr Val Thr Phe Glu Thr Phe Arg Ala Ala Pro Arg
                420                 425                 430

Pro Phe Gly Asn Ala Val Ser Tyr Val Asn Ser Ala Phe Leu Ala Arg
                435                 440                 445

Thr Ser Gly Ser Leu Leu Ile Glu Asp Ile Cys Leu Ala Phe Gly Ala
                450                 455                 460

Tyr Gly Val Asp His Ala Ile Arg Ala Lys Lys Val Glu Asp Phe Leu
465                 470                 475                 480

Lys Gly Lys Ser Leu Ser Ser Phe Val Ile Leu Glu Ala Ile Lys Leu
                485                 490                 495

Leu Lys Asp Thr Val Ser Pro Ser Glu Gly Thr Thr His His Glu Tyr
                500                 505                 510

Arg Val Ser Leu Ala Val Ser Phe Leu Phe Ser Phe Leu Ser Ser Leu
                515                 520                 525

Ala Asn Ser Ser Ser Ala Pro Ser Asn Ile Asp Thr Pro Asn Gly Ser
530                 535                 540

Tyr Thr His Glu Thr Gly Ser Asn Val Asp Ser Pro Glu Arg His Ile
545                 550                 555                 560

Lys Val Asp Ser Asn Asp Leu Pro Ile Arg Ser Arg Gln Glu Met Val
                565                 570                 575

Phe Ser Asp Glu Tyr Lys Pro Val Gly Lys Pro Ile Lys Lys Val Gly
                580                 585                 590

Ala Glu Ile Gln Ala Ser Gly Glu Ala Val Tyr Val Asp Asp Ile Pro
                595                 600                 605

Ala Pro Lys Asp Cys Leu Tyr Gly Ala Phe Ile Tyr Ser Thr His Pro
                610                 615                 620

His Ala His Val Arg Ser Ile Asn Phe Lys Ser Ser Leu Ala Ser Gln
625                 630                 635                 640
```

-continued

```
Lys Val Ile Thr Val Ile Thr Ala Lys Asp Ile Pro Ser Gly Gly Glu
            645                 650                 655

Asn Ile Gly Ser Ser Phe Leu Met Gln Gly Glu Ala Leu Phe Ala Asp
            660                 665                 670

Pro Ile Ala Glu Phe Ala Gly Gln Asn Ile Gly Val Ile Ala Glu
            675                 680                 685

Thr Gln Arg Tyr Ala Asn Met Ala Ala Lys Gln Ala Val Val Glu Tyr
            690                 695                 700

Ser Thr Glu Asn Leu Gln Pro Pro Ile Leu Thr Ile Glu Asp Ala Ile
705                 710                 715                 720

Gln Arg Asn Ser Tyr Ile Gln Ile Pro Pro Phe Leu Ala Pro Lys Pro
                725                 730                 735

Val Gly Asp Tyr Asn Lys Gly Met Ala Glu Ala Asp His Lys Ile Leu
            740                 745                 750

Ser Ala Glu Val Lys Leu Glu Ser Gln Tyr Tyr Phe Tyr Met Glu Thr
            755                 760                 765

Gln Ala Ala Leu Ala Ile Pro Asp Glu Asp Asn Cys Ile Thr Ile Tyr
770                 775                 780

Ser Ser Thr Gln Met Pro Glu Leu Thr Gln Asn Leu Ile Ala Arg Cys
785                 790                 795                 800

Leu Gly Ile Pro Phe His Asn Val Arg Val Ile Ser Arg Arg Val Gly
                805                 810                 815

Gly Gly Phe Gly Gly Lys Ala Met Lys Ala Thr His Thr Ala Cys Ala
                820                 825                 830

Cys Ala Leu Ala Ala Phe Lys Leu Arg Arg Pro Val Arg Met Tyr Leu
            835                 840                 845

Asp Arg Lys Thr Asp Met Ile Met Ala Gly Gly Arg His Pro Met Lys
            850                 855                 860

Ala Lys Tyr Ser Val Gly Phe Lys Ser Asp Gly Lys Ile Thr Ala Leu
865                 870                 875                 880

His Leu Asp Leu Gly Ile Asn Ala Gly Ile Ser Pro Asp Val Ser Pro
                885                 890                 895

Leu Met Pro Arg Ala Ile Ile Gly Ala Leu Lys Lys Tyr Asn Trp Gly
            900                 905                 910

Thr Leu Glu Phe Asp Thr Lys Val Cys Lys Thr Asn Val Ser Ser Lys
            915                 920                 925

Ser Ala Met Arg Ala Pro Gly Asp Val Gln Gly Ser Phe Ile Ala Glu
            930                 935                 940

Ala Ile Ile Glu His Val Ala Ser Ala Leu Ala Leu Asp Thr Asn Thr
945                 950                 955                 960

Val Arg Arg Lys Asn Leu His Asp Phe Glu Ser Leu Glu Val Phe Tyr
                965                 970                 975

Gly Glu Ser Ala Gly Glu Ala Ser Thr Tyr Ser Leu Val Ser Met Phe
            980                 985                 990

Asp Lys Leu Ala Leu Ser Pro Glu Tyr Gln His Arg Ala Ala Met Ile
            995                 1000                1005

Glu Gln Phe Asn Ser Ser Asn Lys Trp Lys Lys Arg Gly Ile Ser Cys
            1010                1015                1020

Val Pro Ala Thr Tyr Glu Val Asn Leu Arg Pro Thr Pro Gly Lys Val
1025                1030                1035                1040

Ser Ile Met Asn Asp Gly Ser Ile Ala Val Glu Val Gly Gly Ile Glu
                1045                1050                1055
```

```
Ile Gly Gln Gly Leu Trp Thr Lys Val Lys Gln Met Thr Ala Phe Gly
             1060                1065                1070
Leu Gly Gln Leu Cys Pro Asp Gly Gly Glu Cys Leu Leu Asp Lys Val
         1075                1080                1085
Arg Val Ile Gln Ala Asp Thr Leu Ser Leu Ile Gln Gly Gly Met Thr
     1090                1095                1100
Ala Gly Ser Thr Thr Ser Glu Thr Ser Cys Glu Thr Val Arg Gln Ser
1105                1110                1115                1120
Cys Val Ala Leu Val Glu Lys Leu Asn Pro Ile Lys Glu Ser Leu Glu
             1125                1130                1135
Ala Lys Ser Asn Thr Val Glu Trp Ser Ala Leu Ile Ala Gln Ala Ser
         1140                1145                1150
Met Ala Ser Val Asn Leu Ser Ala Gln Pro Tyr Trp Thr Pro Asp Pro
         1155                1160                1165
Ser Phe Lys Ser Tyr Leu Asn Tyr Gly Ala Gly Thr Ser Glu Val Glu
     1170                1175                1180
Val Asp Ile Leu Thr Gly Ala Thr Thr Ile Leu Arg Ser Asp Leu Val
1185                1190                1195                1200
Tyr Asp Cys Gly Gln Ser Leu Asn Pro Ala Val Asp Leu Gly Gln Ile
             1205                1210                1215
Glu Gly Cys Phe Val Gln Gly Ile Gly Phe Phe Thr Asn Glu Asp Tyr
         1220                1225                1230
Lys Thr Asn Ser Asp Gly Leu Val Ile His Asp Gly Thr Trp Thr Tyr
     1235                1240                1245
Lys Ile Pro Thr Val Asp Asn Ile Pro Lys Glu Phe Asn Val Glu Met
     1250                1255                1260
Phe Asn Ser Ala Pro Asp Lys Lys Arg Val Leu Ser Ser Lys Ala Ser
1265                1270                1275                1280
Gly Glu Pro Pro Leu Val Leu Ala Thr Ser Val His Cys Ala Met Arg
             1285                1290                1295
Glu Ala Ile Arg Ala Ala Arg Lys Glu Phe Ser Val Ser Thr Ser Pro
         1300                1305                1310
Ala Lys Ser Ala Val Thr Phe Gln Met Asp Val Pro Ala Thr Met Pro
     1315                1320                1325
Val Val Lys Glu Leu Cys Gly Leu Asp Val Val Glu Arg Tyr Leu Glu
1330                1335                1340
Asn Val Ser Ala Ala Ser Ala Gly Pro Asn Thr Ala Lys Ala
1345                1350                1355

(2) INFORMATION FOR SEQ ID NO:3:

(i) SEQUENCE CHARACTERISTICS:
        (A) LENGTH: 4359 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: maize (Zea mays L.)
        (B) STRAIN: cultivar: Golden Cross Bantam 70

(ix) FEATURE:
        (A) NAME/KEY: CDS
        (B) LOCATION: 91..4137

(xi) SEQUENCE DESCRIPTION: SEQ ID NO:3:
```

-continued

| | |
|---|---|
| CCGGCTCTCT CGGTGCAGAC GTCCGGGACT AGTACGTGGA TCGGGCCGGG GGCAACTCGA | 60 |

| | | | | | | | | | | | | | | | | |
|---|---|---|---|---|---|---|---|---|---|---|---|---|---|---|---|---|
| GTCGTCAAGA | AGGCTGCTAC | CTGCTAGAGG | ATG | GAG | ATG | GGG | AAG | GCG | GCG | GCG | | | | | | 114 |
| | | | Met | Glu | Met | Gly | Lys | Ala | Ala | Ala | | | | | | |
| | | | | 1360 | | | | | 1365 | | | | | | | |
| GTG | GTG | CTG | GCG | GTG | AAC | GGC | AAG | CGG | TAC | GAG | GCC | GCC | GGC | GTG | GAC | 162 |
| Val | Val | Leu | Ala | Val | Asn | Gly | Lys | Arg | Tyr | Glu | Ala | Ala | Gly | Val | Asp | |
| | | 1370 | | | | 1375 | | | | 1380 | | | | | | |
| CCG | TCG | ACG | ACG | CTG | CTG | GAG | TTC | CTG | CGC | ACC | CAC | ACG | CCC | GTC | AGG | 210 |
| Pro | Ser | Thr | Thr | Leu | Leu | Glu | Phe | Leu | Arg | Thr | His | Thr | Pro | Val | Arg | |
| | | 1385 | | | | 1390 | | | | 1395 | | | | | | |
| GGG | CCC | AAG | CTC | GGC | TGC | GGC | GAA | GGT | GGC | TGC | GGT | GCA | TGC | GTT | GTG | 258 |
| Gly | Pro | Lys | Leu | Gly | Cys | Gly | Glu | Gly | Gly | Cys | Gly | Ala | Cys | Val | Val | |
| | | 1400 | | | | 1405 | | | | 1410 | | | | | | |
| CTT | GTC | TCG | AAG | TAC | GAC | CCA | GCC | ACC | GAC | GAG | GTG | ACC | GAG | TTC | TCA | 306 |
| Leu | Val | Ser | Lys | Tyr | Asp | Pro | Ala | Thr | Asp | Glu | Val | Thr | Glu | Phe | Ser | |
| 1415 | | | | 1420 | | | | 1425 | | | | 1430 | | | | |
| GCG | AGC | TCC | TGC | CTG | ACG | CTG | CTC | CAT | AGC | GTG | GAC | CGC | TGC | TCG | GTG | 354 |
| Ala | Ser | Ser | Cys | Leu | Thr | Leu | Leu | His | Ser | Val | Asp | Arg | Cys | Ser | Val | |
| | | | | 1435 | | | | 1440 | | | | 1445 | | | | |
| ACC | ACC | AGC | GAG | GGC | ATT | GGC | AAC | ACC | AAG | GAT | GGC | TAC | CAC | CCT | GTG | 402 |
| Thr | Thr | Ser | Glu | Gly | Ile | Gly | Asn | Thr | Lys | Asp | Gly | Tyr | His | Pro | Val | |
| | | 1450 | | | | 1455 | | | | 1460 | | | | | | |
| CAG | CAG | CGC | CTC | TCC | GGC | TTC | CAC | GCC | TCC | CAG | TGC | GGT | TTC | TGC | ACG | 450 |
| Gln | Gln | Arg | Leu | Ser | Gly | Phe | His | Ala | Ser | Gln | Cys | Gly | Phe | Cys | Thr | |
| | | 1465 | | | | 1470 | | | | 1475 | | | | | | |
| CCC | GGC | ATG | TGC | ATG | TCC | ATC | TTC | TCT | GCG | CTT | GTC | AAA | GCC | GAC | AAG | 498 |
| Pro | Gly | Met | Cys | Met | Ser | Ile | Phe | Ser | Ala | Leu | Val | Lys | Ala | Asp | Lys | |
| | | 1480 | | | | 1485 | | | | 1490 | | | | | | |
| GCG | GCC | AAC | CGG | CCA | GCC | CCA | CCG | GCC | GGC | TTC | TCC | AAG | CTC | ACT | TCC | 546 |
| Ala | Ala | Asn | Arg | Pro | Ala | Pro | Pro | Ala | Gly | Phe | Ser | Lys | Leu | Thr | Ser | |
| 1495 | | | | 1500 | | | | 1505 | | | | 1510 | | | | |
| TCG | GAG | GCT | GAG | AAG | GCT | GTC | TCT | GGC | AAC | CTG | TGC | CGC | TGC | ACA | GGG | 594 |
| Ser | Glu | Ala | Glu | Lys | Ala | Val | Ser | Gly | Asn | Leu | Cys | Arg | Cys | Thr | Gly | |
| | | | | 1515 | | | | 1520 | | | | 1525 | | | | |
| TAC | AGG | CCC | ATC | GTC | GAC | GCC | TGT | AAG | AGC | TTC | GCA | GCC | GAT | GTT | GAT | 642 |
| Tyr | Arg | Pro | Ile | Val | Asp | Ala | Cys | Lys | Ser | Phe | Ala | Ala | Asp | Val | Asp | |
| | | | | 1530 | | | | 1535 | | | | 1540 | | | | |
| CTT | GAG | GAC | CTG | GGC | CTC | AAC | TGC | TTC | TGG | AAG | AAG | GGT | GAT | GAG | CCT | 690 |
| Leu | Glu | Asp | Leu | Gly | Leu | Asn | Cys | Phe | Trp | Lys | Lys | Gly | Asp | Glu | Pro | |
| | | | | 1545 | | | | 1550 | | | | 1555 | | | | |
| GCA | GAT | GTC | AGC | AAG | CTG | CCA | GGC | TAC | AAC | AGT | GGT | GAC | GTC | TGC | ACT | 738 |
| Ala | Asp | Val | Ser | Lys | Leu | Pro | Gly | Tyr | Asn | Ser | Gly | Asp | Val | Cys | Thr | |
| | | | | 1560 | | | | 1565 | | | | 1570 | | | | |
| TTC | CCT | GAC | TTT | CTC | AAA | TCT | GAG | ATG | AAG | TCC | TCA | ATT | CAG | CAG | GCT | 786 |
| Phe | Pro | Asp | Phe | Leu | Lys | Ser | Glu | Met | Lys | Ser | Ser | Ile | Gln | Gln | Ala | |
| 1575 | | | | 1580 | | | | 1585 | | | | 1590 | | | | |
| AAC | AGC | GCT | CCA | GTT | CCT | GTT | TCT | GAC | GAC | GGC | TGG | TAC | CGT | CCT | AGG | 834 |
| Asn | Ser | Ala | Pro | Val | Pro | Val | Ser | Asp | Asp | Gly | Trp | Tyr | Arg | Pro | Arg | |
| | | | | 1595 | | | | 1600 | | | | 1605 | | | | |
| AGC | ATT | GAC | GAG | CTT | CAC | AGG | TTG | TTT | CAA | TCT | AGC | TCC | TTC | GAT | GAA | 882 |
| Ser | Ile | Asp | Glu | Leu | His | Arg | Leu | Phe | Gln | Ser | Ser | Ser | Phe | Asp | Glu | |
| | | | | 1610 | | | | 1615 | | | | 1620 | | | | |
| AAT | TCC | GTG | AAG | ATA | GTG | GCT | TCA | AAC | ACT | GGG | TCT | GGA | GTG | TAC | AAG | 930 |
| Asn | Ser | Val | Lys | Ile | Val | Ala | Ser | Asn | Thr | Gly | Ser | Gly | Val | Tyr | Lys | |
| | | | | 1625 | | | | 1630 | | | | 1635 | | | | |
| GAT | CAG | GAC | CTT | TAT | GAC | AAG | TAC | ATT | GAC | ATC | AAA | GGA | ATC | CCA | GAG | 978 |
| Asp | Gln | Asp | Leu | Tyr | Asp | Lys | Tyr | Ile | Asp | Ile | Lys | Gly | Ile | Pro | Glu | |
| | | 1640 | | | | 1645 | | | | 1650 | | | | | | |

```
                                                        -continued

CTT TCA GTC ATC AAC AGA AAC GAC AAA GGA ATT GAG CTT GGA TCA GTT    1026
Leu Ser Val Ile Asn Arg Asn Asp Lys Gly Ile Glu Leu Gly Ser Val
1655                1660                1665                1670

GTG TCC ATC TCT AAA GCT ATT GAG GTG CTG TCA GAT GGA AAT CTC GTC    1074
Val Ser Ile Ser Lys Ala Ile Glu Val Leu Ser Asp Gly Asn Leu Val
                1675                1680                1685

TTC AGA AAG ATT GCT GGT CAC CTG AAC AAA GTG GCT TCA CCG TTT GTT    1122
Phe Arg Lys Ile Ala Gly His Leu Asn Lys Val Ala Ser Pro Phe Val
            1690                1695                1700

CGG AAC ACT GCA ACC ATA GGT GGA AAC ATA GTC ATG GCA CAA AGA TTG    1170
Arg Asn Thr Ala Thr Ile Gly Gly Asn Ile Val Met Ala Gln Arg Leu
        1705                1710                1715

CCA TTC GCA TCG GAC ATT GCA ACC ATA CTA CTA GCT GCA GGT TCA ACA    1218
Pro Phe Ala Ser Asp Ile Ala Thr Ile Leu Leu Ala Ala Gly Ser Thr
    1720                1725                1730

GTC ACA ATC CAG GTG GCT TCC AAA AGG CTG TGC TTC ACT CTG GAG GAG    1266
Val Thr Ile Gln Val Ala Ser Lys Arg Leu Cys Phe Thr Leu Glu Glu
1735                1740                1745                1750

TTC TTG CAG CAG CCT CCA TGC GAT TCT AGG ACC CTG CTG CTG AGC ATA    1314
Phe Leu Gln Gln Pro Pro Cys Asp Ser Arg Thr Leu Leu Leu Ser Ile
                1755                1760                1765

TTT ATC CCG GAA TGG GGC TCA AAT GAT GTC ACC TTT GAG ACT TTC CGA    1362
Phe Ile Pro Glu Trp Gly Ser Asn Asp Val Thr Phe Glu Thr Phe Arg
            1770                1775                1780

GCA GCA CCT CGT CCA CTT GGC AAT GCT GTC TCA TAT GTC AAT TCA GCT    1410
Ala Ala Pro Arg Pro Leu Gly Asn Ala Val Ser Tyr Val Asn Ser Ala
        1785                1790                1795

TTC TTG GCA AGG ACT TCA TTG GAT GCA GCA TCA AAG GAC CAT CTC ATC    1458
Phe Leu Ala Arg Thr Ser Leu Asp Ala Ala Ser Lys Asp His Leu Ile
    1800                1805                1810

GAG GAT ATA TGT CTG GCG TTC GGT GCT TAT GGA GCT GAT CAT GCT ATT    1506
Glu Asp Ile Cys Leu Ala Phe Gly Ala Tyr Gly Ala Asp His Ala Ile
1815                1820                1825                1830

AGA GCT AGA AAG GTT GAG GAT TAC CTG AAG GGC AAA ACA GTG AGC TCG    1554
Arg Ala Arg Lys Val Glu Asp Tyr Leu Lys Gly Lys Thr Val Ser Ser
                1835                1840                1845

TCT GTC ATA CTT GAA GCT GTT CGG TTG CTT AAA GGG TCT ATT AAA CCA    1602
Ser Val Ile Leu Glu Ala Val Arg Leu Leu Lys Gly Ser Ile Lys Pro
            1850                1855                1860

TCA GAA GGC TCA ACA CAT CCT GAG TAT AGA ATT AGC TTG GCT GTC AGT    1650
Ser Glu Gly Ser Thr His Pro Glu Tyr Arg Ile Ser Leu Ala Val Ser
        1865                1870                1875

TTC TTG TTT ACC TTC CTA TCC TCC CTT GCC AAC AGC TTG AAT GAA TCT    1698
Phe Leu Phe Thr Phe Leu Ser Ser Leu Ala Asn Ser Leu Asn Glu Ser
    1880                1885                1890

GCA AAG GTT AGT GGT ACC AAC GAG CAC TCA CCA GAG AAG CAA CTC AAG    1746
Ala Lys Val Ser Gly Thr Asn Glu His Ser Pro Glu Lys Gln Leu Lys
1895                1900                1905                1910

TTG GAC ATC AAT GAT TTG CCA ATA CGA TCA AGA CAA GAA ATA TTT TTC    1794
Leu Asp Ile Asn Asp Leu Pro Ile Arg Ser Arg Gln Glu Ile Phe Phe
                1915                1920                1925

ACT GAT GCA TAT AAG CCA GTT GGC AAA GCA ATT AAG AAA GCT GGG GTA    1842
Thr Asp Ala Tyr Lys Pro Val Gly Lys Ala Ile Lys Lys Ala Gly Val
            1930                1935                1940

GAG ATC CAA GCT TCA GGG GAA GCT GTG TAC GTT GAT GAT ATC CCT GCT    1890
Glu Ile Gln Ala Ser Gly Glu Ala Val Tyr Val Asp Asp Ile Pro Ala
        1945                1950                1955

CCC AAA GAT TGC CTC TAT GGG GCA TTT ATT TAT AGC ACA CAC CCT CAT    1938
Pro Lys Asp Cys Leu Tyr Gly Ala Phe Ile Tyr Ser Thr His Pro His
    1960                1965                1970
```

-continued

```
GCA CAT GTA AAG TCA ATC AAC TTT AAA CCA TCT TTG GCT TCA CAG AAG       1986
Ala His Val Lys Ser Ile Asn Phe Lys Pro Ser Leu Ala Ser Gln Lys
1975              1980                1985                1990

ATC ATC ACA GTT ATC ACT GCA AAG GAT ATT CCC AGC GGT GGA CAA AAT       2034
Ile Ile Thr Val Ile Thr Ala Lys Asp Ile Pro Ser Gly Gly Gln Asn
              1995                2000                2005

GTT GGT TAT AGC TTC CCG ATG ATT GGA GAA GAA GCA CTT TTT GCA GAT       2082
Val Gly Tyr Ser Phe Pro Met Ile Gly Glu Glu Ala Leu Phe Ala Asp
            2010                2015                2020

CCA GTT GCT GAA TTT GCT GGT CAA AAT ATT GGT GTC GTG ATT GCT CAA       2130
Pro Val Ala Glu Phe Ala Gly Gln Asn Ile Gly Val Val Ile Ala Gln
        2025                2030                2035

ACA CAG AAG TAT GCC TAC ATG GCG GCA AAG CAA GCC ATC ATT GAG TAT       2178
Thr Gln Lys Tyr Ala Tyr Met Ala Ala Lys Gln Ala Ile Ile Glu Tyr
    2040                2045                2050

AGC ACA GAA AAT CTG CAG CCA CCA ATT CTG ACA ATA GAA GAT GCA ATT       2226
Ser Thr Glu Asn Leu Gln Pro Pro Ile Leu Thr Ile Glu Asp Ala Ile
2055                2060                2065                2070

GAA CGA AGC AGC TTC TTC CAA ACC CTC CCA TTT GTA GCT CCT AAG CCA       2274
Glu Arg Ser Ser Phe Phe Gln Thr Leu Pro Phe Val Ala Pro Lys Pro
              2075                2080                2085

GTT GGT GAT TAC GAC AAA GGG ATG TCT GAA GCT GAT CAC AAG ATT TTA       2322
Val Gly Asp Tyr Asp Lys Gly Met Ser Glu Ala Asp His Lys Ile Leu
            2090                2095                2100

TCG GCA GAG GTA AAA ATT GAA TCC CAA TAC TTT TTC TAC ATG GAG CCA       2370
Ser Ala Glu Val Lys Ile Glu Ser Gln Tyr Phe Phe Tyr Met Glu Pro
        2105                2110                2115

CAA GTG GCG CTA GCT ATT CCT GAT GAA GAT AAC TGC ATA ACC ATC TAT       2418
Gln Val Ala Leu Ala Ile Pro Asp Glu Asp Asn Cys Ile Thr Ile Tyr
    2120                2125                2130

TTT TCG ACA CAA TTA CCT GAG TCC ACA CAA AAT GTG GTT GCA AAG TGC       2466
Phe Ser Thr Gln Leu Pro Glu Ser Thr Gln Asn Val Val Ala Lys Cys
2135                2140                2145                2150

GTT GGC ATT CCA TTT CAC AAT GTC CGT GTA ATC ACC AGA AGG GTC GGA       2514
Val Gly Ile Pro Phe His Asn Val Arg Val Ile Thr Arg Arg Val Gly
              2155                2160                2165

GGA GGC TTT GGT GGA AAA GCA TTG AAA TCA ATG CAT GTT GCA TGT GCA       2562
Gly Gly Phe Gly Gly Lys Ala Leu Lys Ser Met His Val Ala Cys Ala
            2170                2175                2180

TGT GCA GTT GCT GCA TTG AAG CTA CAA CGT CCA GTT CGG ATG TAC CTC       2610
Cys Ala Val Ala Ala Leu Lys Leu Gln Arg Pro Val Arg Met Tyr Leu
        2185                2190                2195

GAT CGC AAG ACA GAC ATG ATA ATG GCA GGC GGG CGG CAT CCT ATG AAG       2658
Asp Arg Lys Thr Asp Met Ile Met Ala Gly Gly Arg His Pro Met Lys
    2200                2205                2210

GTG AAG TAC TCT GTT GGG TTC AAG TCA AAC GGC AAG ATC ACA GCC TTA       2706
Val Lys Tyr Ser Val Gly Phe Lys Ser Asn Gly Lys Ile Thr Ala Leu
2215                2220                2225                2230

CAT CTT GAT CTT GGG ATC AAT GGT GGA ATA TCT CCA GAT ATG AGT CCA       2754
His Leu Asp Leu Gly Ile Asn Gly Gly Ile Ser Pro Asp Met Ser Pro
              2235                2240                2245

ATG ATT GCA GCA CCT GTC ATA GGT TCT CTC AAA AAG TAC AAC TGG GGC       2802
Met Ile Ala Ala Pro Val Ile Gly Ser Leu Lys Lys Tyr Asn Trp Gly
            2250                2255                2260

AAT CTT GCA TTT GAC ACC AAG GTC TGC AAA ACA AAT GTC TCA TCA AAA       2850
Asn Leu Ala Phe Asp Thr Lys Val Cys Lys Thr Asn Val Ser Ser Lys
        2265                2270                2275

TCG TCA ATG AGA GCT CCT GGA GAT GCG CAG GGC TCT TTC ATT GCT GAA       2898
Ser Ser Met Arg Ala Pro Gly Asp Ala Gln Gly Ser Phe Ile Ala Glu
```

```
                    2280              2285              2290
GCC ATC ATC GAG CAT GTT GCC TCG GCA CTT TCA GCC GAC ACT AAT ACC      2946
Ala Ile Ile Glu His Val Ala Ser Ala Leu Ser Ala Asp Thr Asn Thr
2295                2300              2305              2310

ATA AGG AGA AAG AAC CTT CAT GAC TTT GAG AGC CTT GCA GTG TTC TTT      2994
Ile Arg Arg Lys Asn Leu His Asp Phe Glu Ser Leu Ala Val Phe Phe
            2315              2320              2325

GGA GAT AGT GCA GGT GAA GCT TCT ACA TAC AGC CTT GTC ACC ATG TTC      3042
Gly Asp Ser Ala Gly Glu Ala Ser Thr Tyr Ser Leu Val Thr Met Phe
        2330              2335              2340

GAT AAA TTG GCC TCC TCT CCA GAA TAC CAG CAC CGA GCT GAA ATG GTG      3090
Asp Lys Leu Ala Ser Ser Pro Glu Tyr Gln His Arg Ala Glu Met Val
    2345              2350              2355

GAA CAA TTC AAC CGA AGC AAC AAG TGG AAG AAG CGT GGC ATT TCT TGT      3138
Glu Gln Phe Asn Arg Ser Asn Lys Trp Lys Lys Arg Gly Ile Ser Cys
2360              2365              2370

GTG CCT GTA ACA TAT GAG GTG CAG CTT CGG CCA ACT CCA GGA AAG GTG      3186
Val Pro Val Thr Tyr Glu Val Gln Leu Arg Pro Thr Pro Gly Lys Val
2375              2380              2385              2390

TCT ATC ATG AAT GAT GGT TCC ATT GCT GTT GAG GTT GGA GGG GTT GAG      3234
Ser Ile Met Asn Asp Gly Ser Ile Ala Val Glu Val Gly Gly Val Glu
            2395              2400              2405

CTA GGC CAA GGG TTG TGG ACA AAA GTG AAG CAG ATG ACG GCA TTC GGA      3282
Leu Gly Gln Gly Leu Trp Thr Lys Val Lys Gln Met Thr Ala Phe Gly
        2410              2415              2420

CTA GGA CAG CTG TGT CCT GGC GGC GGT GAA AGC CTT CTA GAC AAG GTG      3330
Leu Gly Gln Leu Cys Pro Gly Gly Gly Glu Ser Leu Leu Asp Lys Val
    2425              2430              2435

CGG GTC ATC CAG GCC GAC ACA TTG AGC ATG ATC CAA GGA GGG GTC ACT      3378
Arg Val Ile Gln Ala Asp Thr Leu Ser Met Ile Gln Gly Gly Val Thr
2440              2445              2450

GGT GGG AGC ACC ACT TCT GAA ACT AGC TGT GAA GCA GTT CGT AAG TCG      3426
Gly Gly Ser Thr Thr Ser Glu Thr Ser Cys Glu Ala Val Arg Lys Ser
2455              2460              2465              2470

TGT GTT GCA CTC GTC GAG AGC TTG AAG CCA ATC AAG GAG AAT CTG GAG      3474
Cys Val Ala Leu Val Glu Ser Leu Lys Pro Ile Lys Glu Asn Leu Glu
            2475              2480              2485

GCT AAA ACT GGC ACA GTG GAA TGG AGT GCC TTG ATT GCA CAG GCA AGT      3522
Ala Lys Thr Gly Thr Val Glu Trp Ser Ala Leu Ile Ala Gln Ala Ser
        2490              2495              2500

ATG GCG AGC GTT AAC TTA TCG GCA CAT GCA TAC TGG ACC CCT GAT CCA      3570
Met Ala Ser Val Asn Leu Ser Ala His Ala Tyr Trp Thr Pro Asp Pro
    2505              2510              2515

ACT TTC ACA AGC TAT TTG AAC TAC GGA GCC GGC ACT AGC GAG GTG GAA      3618
Thr Phe Thr Ser Tyr Leu Asn Tyr Gly Ala Gly Thr Ser Glu Val Glu
2520              2525              2530

ATT GAT GTC CTG ACA GGA GCA ACA ACA ATT CTA AGG AGT GAC CTT GTC      3666
Ile Asp Val Leu Thr Gly Ala Thr Thr Ile Leu Arg Ser Asp Leu Val
2535              2540              2545              2550

TAC GAT TGC GGG CAA AGC TTG AAC CCT GCT GTC GAT TTG GGG CAG GTG      3714
Tyr Asp Cys Gly Gln Ser Leu Asn Pro Ala Val Asp Leu Gly Gln Val
            2555              2560              2565

GAA GGT GCA TTC GTA CAA GGA GTA GGC TTC TTC ACA AAC GAG GAG TAC      3762
Glu Gly Ala Phe Val Gln Gly Val Gly Phe Phe Thr Asn Glu Glu Tyr
        2570              2575              2580

GCA ACC AAC TCT GAC GGG TTG GTC ATC CAC GAT GGC ACA TGG ACG TAC      3810
Ala Thr Asn Ser Asp Gly Leu Val Ile His Asp Gly Thr Trp Thr Tyr
    2585              2590              2595

AAG ATC CCC ACG GTC GAC ACC ATC CCA AAG CAG TTC AAC GTT GAG CTG      3858
```

-continued

```
Lys Ile Pro Thr Val Asp Thr Ile Pro Lys Gln Phe Asn Val Glu Leu
2600                2605                2610

ATC AAC AGC GCC CGT GAC CAG AAG CGC GTC CTC TCT TCC AAA GCA TCG    3906
Ile Asn Ser Ala Arg Asp Gln Lys Arg Val Leu Ser Ser Lys Ala Ser
2615                2620                2625                2630

GGC GAG CCT CCG CTT CTC CTA GCT TCC TCT GTG CAC TGC GCA ATG AGG    3954
Gly Glu Pro Pro Leu Leu Leu Ala Ser Ser Val His Cys Ala Met Arg
                2635                2640                2645

GAG GCC ATC AGG GCC GCC AGG AAA GAA TTC TCG GTC TGC ACT GGT CCA    4002
Glu Ala Ile Arg Ala Ala Arg Lys Glu Phe Ser Val Cys Thr Gly Pro
2650                2655                2660

GCG AAC TCC GCC ATC ACG TTC CAG ATG GAC GTG CCG GCA ACG ATG CCT    4050
Ala Asn Ser Ala Ile Thr Phe Gln Met Asp Val Pro Ala Thr Met Pro
                2665                2670                2675

GTC GTC AAG GAG CTC TGC GGC CTG GAT GTC GTT GAG AGG TAC CTG GAG    4098
Val Val Lys Glu Leu Cys Gly Leu Asp Val Val Glu Arg Tyr Leu Glu
2680                2685                2690

AGC GTG TCG GCT GCC AGC CCA ACA AAC ACC GCT AAA GCA TAGATCCAGT     4147
Ser Val Ser Ala Ala Ser Pro Thr Asn Thr Ala Lys Ala
2695                2700                2705

AGGCGCTCTA TCCATGGTGT GATGGCTTAA TCAATCTGTA AAACACTAAG CGGCGTGACA  4207

TGCCGAGCTT TCAGTGTTAG CTATGATGTA CAGAAGAAGA GGTACCAATG GCGAGTTGTG  4267

GCCATGCGAA TCAGGAGTCA TGAACCATTG AGGGGGGAAA TAAAGTAAAT AAGTGTTGCG  4327

CCGGCGAAAA AAAAAAAAAA AAAAAAAAAA AA                                4359
```

(2) INFORMATION FOR SEQ ID NO:4:

(i) SEQUENCE CHARACTERISTICS:
        (A) LENGTH: 1349 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Met Gly Lys Ala Ala Val Val Leu Ala Val Asn Gly Lys
1               5                   10                  15

Arg Tyr Glu Ala Ala Gly Val Asp Pro Ser Thr Thr Leu Leu Glu Phe
                20                  25                  30

Leu Arg Thr His Thr Pro Val Arg Gly Pro Lys Leu Gly Cys Gly Glu
            35                  40                  45

Gly Gly Cys Gly Ala Cys Val Val Leu Val Ser Lys Tyr Asp Pro Ala
        50                  55                  60

Thr Asp Glu Val Thr Glu Phe Ser Ala Ser Ser Cys Leu Thr Leu Leu
65                  70                  75                  80

His Ser Val Asp Arg Cys Ser Val Thr Thr Ser Glu Gly Ile Gly Asn
                85                  90                  95

Thr Lys Asp Gly Tyr His Pro Val Gln Gln Arg Leu Ser Gly Phe His
                100                 105                 110

Ala Ser Gln Cys Gly Phe Cys Thr Pro Gly Met Cys Met Ser Ile Phe
            115                 120                 125

Ser Ala Leu Val Lys Ala Asp Lys Ala Ala Asn Arg Pro Ala Pro Pro
130                 135                 140

Ala Gly Phe Ser Lys Leu Thr Ser Ser Glu Ala Glu Lys Ala Val Ser
145                 150                 155                 160

Gly Asn Leu Cys Arg Cys Thr Gly Tyr Arg Pro Ile Val Asp Ala Cys
                165                 170                 175
```

```
Lys Ser Phe Ala Ala Asp Val Asp Leu Glu Asp Leu Gly Leu Asn Cys
            180                 185                 190

Phe Trp Lys Lys Gly Asp Glu Pro Ala Asp Val Ser Lys Leu Pro Gly
        195                 200                 205

Tyr Asn Ser Gly Asp Val Cys Thr Phe Pro Asp Phe Leu Lys Ser Glu
        210                 215                 220

Met Lys Ser Ser Ile Gln Gln Ala Asn Ser Ala Pro Val Pro Val Ser
225                 230                 235                 240

Asp Asp Gly Trp Tyr Arg Pro Arg Ser Ile Asp Glu Leu His Arg Leu
                245                 250                 255

Phe Gln Ser Ser Ser Phe Asp Glu Asn Ser Val Lys Ile Val Ala Ser
                260                 265                 270

Asn Thr Gly Ser Gly Val Tyr Lys Asp Gln Asp Leu Tyr Asp Lys Tyr
            275                 280                 285

Ile Asp Ile Lys Gly Ile Pro Glu Leu Ser Val Ile Asn Arg Asn Asp
        290                 295                 300

Lys Gly Ile Glu Leu Gly Ser Val Val Ser Ile Ser Lys Ala Ile Glu
305                 310                 315                 320

Val Leu Ser Asp Gly Asn Leu Val Phe Arg Lys Ile Ala Gly His Leu
                325                 330                 335

Asn Lys Val Ala Ser Pro Phe Val Arg Asn Thr Ala Thr Ile Gly Gly
            340                 345                 350

Asn Ile Val Met Ala Gln Arg Leu Pro Phe Ala Ser Asp Ile Ala Thr
            355                 360                 365

Ile Leu Leu Ala Ala Gly Ser Thr Val Thr Ile Gln Val Ala Ser Lys
        370                 375                 380

Arg Leu Cys Phe Thr Leu Glu Glu Phe Leu Gln Gln Pro Pro Cys Asp
385                 390                 395                 400

Ser Arg Thr Leu Leu Leu Ser Ile Phe Ile Pro Glu Trp Gly Ser Asn
                405                 410                 415

Asp Val Thr Phe Glu Thr Phe Arg Ala Ala Pro Arg Pro Leu Gly Asn
            420                 425                 430

Ala Val Ser Tyr Val Asn Ser Ala Phe Leu Ala Arg Thr Ser Leu Asp
            435                 440                 445

Ala Ala Ser Lys Asp His Leu Ile Glu Asp Ile Cys Leu Ala Phe Gly
        450                 455                 460

Ala Tyr Gly Ala Asp His Ala Ile Arg Ala Arg Lys Val Glu Asp Tyr
465                 470                 475                 480

Leu Lys Gly Lys Thr Val Ser Ser Val Ile Leu Glu Ala Val Arg
                485                 490                 495

Leu Leu Lys Gly Ser Ile Lys Pro Ser Glu Gly Ser Thr His Pro Glu
            500                 505                 510

Tyr Arg Ile Ser Leu Ala Val Ser Phe Leu Phe Thr Phe Leu Ser Ser
        515                 520                 525

Leu Ala Asn Ser Leu Asn Glu Ser Ala Lys Val Ser Gly Thr Asn Glu
        530                 535                 540

His Ser Pro Glu Lys Gln Leu Lys Leu Asp Ile Asn Asp Leu Pro Ile
545                 550                 555                 560

Arg Ser Arg Gln Glu Ile Phe Phe Thr Asp Ala Tyr Lys Pro Val Gly
                565                 570                 575

Lys Ala Ile Lys Lys Ala Gly Val Glu Ile Gln Ala Ser Gly Glu Ala
            580                 585                 590
```

-continued

```
Val Tyr Val Asp Asp Ile Pro Ala Pro Lys Asp Cys Leu Tyr Gly Ala
        595                 600                 605

Phe Ile Tyr Ser Thr His Pro His Ala His Val Lys Ser Ile Asn Phe
    610                 615                 620

Lys Pro Ser Leu Ala Ser Gln Lys Ile Ile Thr Val Ile Thr Ala Lys
625                 630                 635                 640

Asp Ile Pro Ser Gly Gly Gln Asn Val Gly Tyr Ser Phe Pro Met Ile
                645                 650                 655

Gly Glu Glu Ala Leu Phe Ala Asp Pro Val Ala Glu Phe Ala Gly Gln
                660                 665                 670

Asn Ile Gly Val Val Ile Ala Gln Thr Gln Lys Tyr Ala Tyr Met Ala
            675                 680                 685

Ala Lys Gln Ala Ile Ile Glu Tyr Ser Thr Glu Asn Leu Gln Pro Pro
    690                 695                 700

Ile Leu Thr Ile Glu Asp Ala Ile Glu Arg Ser Ser Phe Phe Gln Thr
705                 710                 715                 720

Leu Pro Phe Val Ala Pro Lys Pro Val Gly Asp Tyr Asp Lys Gly Met
                725                 730                 735

Ser Glu Ala Asp His Lys Ile Leu Ser Ala Glu Val Lys Ile Glu Ser
                740                 745                 750

Gln Tyr Phe Phe Tyr Met Glu Pro Gln Val Ala Leu Ala Ile Pro Asp
    755                 760                 765

Glu Asp Asn Cys Ile Thr Ile Tyr Phe Ser Thr Gln Leu Pro Glu Ser
770                 775                 780

Thr Gln Asn Val Val Ala Lys Cys Val Gly Ile Pro Phe His Asn Val
785                 790                 795                 800

Arg Val Ile Thr Arg Arg Val Gly Gly Phe Gly Gly Lys Ala Leu
                805                 810                 815

Lys Ser Met His Val Ala Cys Ala Cys Ala Val Ala Ala Leu Lys Leu
                820                 825                 830

Gln Arg Pro Val Arg Met Tyr Leu Asp Arg Lys Thr Asp Met Ile Met
    835                 840                 845

Ala Gly Gly Arg His Pro Met Lys Val Lys Tyr Ser Val Gly Phe Lys
850                 855                 860

Ser Asn Gly Lys Ile Thr Ala Leu His Leu Asp Leu Gly Ile Asn Gly
865                 870                 875                 880

Gly Ile Ser Pro Asp Met Ser Pro Met Ile Ala Ala Pro Val Ile Gly
                885                 890                 895

Ser Leu Lys Lys Tyr Asn Trp Gly Asn Leu Ala Phe Asp Thr Lys Val
        900                 905                 910

Cys Lys Thr Asn Val Ser Ser Lys Ser Ser Met Arg Ala Pro Gly Asp
    915                 920                 925

Ala Gln Gly Ser Phe Ile Ala Glu Ala Ile Glu His Val Ala Ser
    930                 935                 940

Ala Leu Ser Ala Asp Thr Asn Thr Ile Arg Arg Lys Asn Leu His Asp
945                 950                 955                 960

Phe Glu Ser Leu Ala Val Phe Phe Gly Asp Ser Ala Gly Glu Ala Ser
                965                 970                 975

Thr Tyr Ser Leu Val Thr Met Phe Asp Lys Leu Ala Ser Ser Pro Glu
                980                 985                 990

Tyr Gln His Arg Ala Glu Met Val Glu Gln Phe Asn Arg Ser Asn Lys
        995                 1000                1005

Trp Lys Lys Arg Gly Ile Ser Cys Val Pro Val Thr Tyr Glu Val Gln
```

-continued

```
            1010                1015                1020
Leu Arg Pro Thr Pro Gly Lys Val Ser Ile Met Asn Asp Gly Ser Ile
1025                1030                1035                1040

Ala Val Glu Val Gly Gly Val Glu Leu Gly Gln Gly Leu Trp Thr Lys
                    1045                1050                1055

Val Lys Gln Met Thr Ala Phe Gly Leu Gly Gln Leu Cys Pro Gly Gly
            1060                1065                1070

Gly Glu Ser Leu Leu Asp Lys Val Arg Val Ile Gln Ala Asp Thr Leu
                1075                1080                1085

Ser Met Ile Gln Gly Gly Val Thr Gly Gly Ser Thr Thr Ser Glu Thr
            1090                1095                1100

Ser Cys Glu Ala Val Arg Lys Ser Cys Val Ala Leu Val Glu Ser Leu
1105                1110                1115                1120

Lys Pro Ile Lys Glu Asn Leu Glu Ala Lys Thr Gly Thr Val Glu Trp
                    1125                1130                1135

Ser Ala Leu Ile Ala Gln Ala Ser Met Ala Ser Val Asn Leu Ser Ala
                1140                1145                1150

His Ala Tyr Trp Thr Pro Asp Pro Thr Phe Thr Ser Tyr Leu Asn Tyr
                1155                1160                1165

Gly Ala Gly Thr Ser Glu Val Glu Ile Asp Val Leu Thr Gly Ala Thr
                1170                1175                1180

Thr Ile Leu Arg Ser Asp Leu Val Tyr Asp Cys Gly Gln Ser Leu Asn
1185                1190                1195                1200

Pro Ala Val Asp Leu Gly Gln Val Glu Gly Ala Phe Val Gln Gly Val
                1205                1210                1215

Gly Phe Phe Thr Asn Glu Glu Tyr Ala Thr Asn Ser Asp Gly Leu Val
                1220                1225                1230

Ile His Asp Gly Thr Trp Thr Tyr Lys Ile Pro Thr Val Asp Thr Ile
                1235                1240                1245

Pro Lys Gln Phe Asn Val Glu Leu Ile Asn Ser Ala Arg Asp Gln Lys
            1250                1255                1260

Arg Val Leu Ser Ser Lys Ala Ser Gly Glu Pro Pro Leu Leu Leu Ala
1265                1270                1275                1280

Ser Ser Val His Cys Ala Met Arg Glu Ala Ile Arg Ala Ala Arg Lys
                1285                1290                1295

Glu Phe Ser Val Cys Thr Gly Pro Ala Asn Ser Ala Ile Thr Phe Gln
            1300                1305                1310

Met Asp Val Pro Ala Thr Met Pro Val Val Lys Glu Leu Cys Gly Leu
            1315                1320                1325

Asp Val Val Glu Arg Tyr Leu Glu Ser Val Ser Ala Ala Ser Pro Thr
            1330                1335                1340

Asn Thr Ala Lys Ala
1345
```

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (23-mer in anti-sense orientation)"

(ix) FEATURE:

```
            (A) NAME/KEY: modified_base
            (B) LOCATION: 6
            (D) OTHER INFORMATION: /mod_base= i (ix) FEATURE:
            (A) NAME/KEY: modified_base
            (B) LOCATION: 9
            (D) OTHER INFORMATION: /mod_base= i (ix) FEATURE:
            (A) NAME/KEY: modified_base
            (B) LOCATION: 18
            (D) OTHER INFORMATION: /mod_base= i (ix) FEATURE:
            (A) NAME/KEY: modified_base
            (B) LOCATION: 21
            (D) OTHER INFORMATION: /mod_base= i (xi) SEQUENCE DESCRIPTION: SEQ ID NO:5:

GTCCANGTNC CRTCTTGNAT NAC                                              23

(2) INFORMATION FOR SEQ ID NO:6:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer
                (23-mer in sense orientation)"

(ix) FEATURE:
            (A) NAME/KEY: modified_base
            (B) LOCATION: 3
            (D) OTHER INFORMATION: /mod_base= i (ix) FEATURE:
            (A) NAME/KEY: modified_base
            (B) LOCATION: 9
            (D) OTHER INFORMATION: /mod_base= i (ix) FEATURE:
            (A) NAME/KEY: modified_base
            (B) LOCATION: 12
            (D) OTHER INFORMATION: /mod_base= i (ix) FEATURE:
            (A) NAME/KEY: modified_base
            (B) LOCATION: 18
            (D) OTHER INFORMATION: /mod_base= i (xi) SEQUENCE DESCRIPTION: SEQ ID NO:6:

GGNGARGCNG TNTAYGTNGA YGA                                              23

(2) INFORMATION FOR SEQ ID NO:7:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "oligonucleotide primer
                (sense)"

(xi) SEQUENCE DESCRIPTION: SEQ ID NO:7:

GCTGGTCAAA ATATTGGTGT CGTGATTG                                         28

(2) INFORMATION FOR SEQ ID NO:8:
```

-continued (i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (sense)"

(xi) SEQUENCE DESCRIPTION: SEQ ID NO:8:

GATTGCTGAA ACACAAAGAT ATGCTAAT                                28

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (anti-sense)"

(xi) SEQUENCE DESCRIPTION: SEQ ID NO:9:

TGGCTGCAGA TTTTCTGTGC TATACTC                                 27

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (anti-sense)"

(xi) SEQUENCE DESCRIPTION: SEQ ID NO:10:

TGCTTTGCAG CCATATTAGC ATATCTT                                 27

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (anti-sense)"

(xi) SEQUENCE DESCRIPTION: SEQ ID NO:11:

ACAGCCTTTT GGAAGCCACC TGGA                                    24

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (anti-sense)"

```
(xi) SEQUENCE DESCRIPTION: SEQ ID NO:12:

ATCGGACTTG TTGTCGGCCT TGAC                                              24

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (sense)"

(xi) SEQUENCE DESCRIPTION: SEQ ID NO:13:

GATTGCTCAA ACACAGAAGT ATGCCTAC                                          28

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (anti-sense)"

(xi) SEQUENCE DESCRIPTION: SEQ ID NO:14:

CTTTGCCGCC ATGTAGGCAT ACTTC                                             25

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "oligonucleotide primer
            (anti-sense)"

(xi) SEQUENCE DESCRIPTION: SEQ ID NO:15:

TTCCACCTAT GGTTGCAGTG TTCC                                              24
```